United States Patent

Corbier et al.

[11] Patent Number: 5,977,155
[45] Date of Patent: *Nov. 2, 1999

[54] IMIDAZOLE-5-CARBOXAMIDES

[75] Inventors: Alain Corbier, Verrieres-le-Buisson; Pierre Deprez, Thiais; Michel Fortin, Paris; Jacques Guillaume, Livry-Gargan; Bertrand Heckmann, Cachan, all of France

[73] Assignee: Hoechst Marion Roussel, France

[*] Notice: This patent is subject to a terminal disclaimer.

[21] Appl. No.: 09/088,156

[22] Filed: Jun. 1, 1998

Related U.S. Application Data

[62] Division of application No. 08/700,468, filed as application No. PCT/FR95/00228, Feb. 27, 1995, Pat. No. 5,811,445.

[30] Foreign Application Priority Data

Mar. 4, 1994 [FR] France .................................. 94/02518

[51] Int. Cl.⁶ ...................... A61K 31/415; C07D 233/02; C07D 233/38; C07D 233/40
[52] U.S. Cl. .......................... 514/398; 514/399; 514/400; 548/315.1; 548/317.1; 548/322.5; 548/333.5; 548/335.5; 548/343.1; 548/343.5; 548/346.1
[58] Field of Search .................. 548/333.5, 335.5, 548/315.1, 317.1, 322.5, 343.5, 346.1; 514/399, 398, 400

[56] References Cited

U.S. PATENT DOCUMENTS

| 5,527,919 | 6/1996 | Bhatnagar et al. .................. 548/250 |
| 5,811,445 | 9/1998 | Corbier et al. ........................ 514/398 |

FOREIGN PATENT DOCUMENTS

| 0324377 | 7/1989 | European Pat. Off. . |
| 0409332 | 1/1991 | European Pat. Off. . |
| 0479479 | 4/1992 | European Pat. Off. . |
| 0503162 | 9/1992 | European Pat. Off. . |
| 0505098 | 9/1992 | European Pat. Off. . |
| 0560177 | 9/1993 | European Pat. Off. . |
| 0577023 | 1/1994 | European Pat. Off. . |
| 0577025 | 1/1994 | European Pat. Off. . |
| 0465368 | 1/1992 | France . |
| 91-07253 | 10/1991 | WIPO . |
| 91-05717 | 12/1994 | WIPO . |

OTHER PUBLICATIONS

Pharmacology vol. 120, p. 21 Biorganic & Medical, 1994.
Chemistry Letters, vol. 4, No. 1, pp. 69–74, 1994.

Primary Examiner—Floyd D. Higel
Attorney, Agent, or Firm—Bierman, Muserlian and Lucas

[57] ABSTRACT

Products of formula (1), wherein $R_1$ is particularly

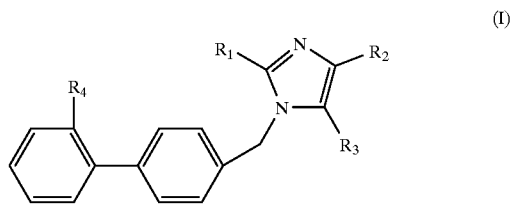

alkyl, alkylthio or alkoxy; $R_2$ is particularly halogen, —S—R, —O—R or —C(OH)(R)—COOH, where R is alkyl or alkenyl; $R_3$ is particularly carboxy, acyl, halogen, alkyl, alkenyl or alkylthio; and $R_4$ is particularly —$(CH_2)_{m1}$—COOR$_4$, —$(CH_2)_{m1}$—CONHR$_{14}$, —$(CH_2)_{m1}$—CN, —$SO_2$—NH—$SO_2$—R$_{14}$, 13 NH—$SO_2$—R$_{14}$, —PO$_3$R$_{14}$, or —NH—$SO_2$—CF$_3$, where m1 is 0–4 and $R_{14}$ is hydrogen, alkyl or alkenyl; are useful for preparing pharmaceutical compositions for treating disorders resulting from abnormal stimulation of angiotensin II receptors $AT_1$ and $AT_2$.

5 Claims, No Drawings

IMIDAZOLE-5-CARBOXAMIDES

PRIOR APPLICATION

This application is a division of U.S. patent application Ser. No. 700,468 filed Aug. 30, 1996, now U.S. Pat. No. 5,811,455, which is a 371 of PCT/FR95/00228, filed Feb. 27, 1995.

The present invention relates to a new use of imidazole derivatives for the treatment of illnesses involving the $AT_1$ and $AT_2$ receptors of angiotensin, some of these products, their preparation, their use as medicaments and the pharmaceutical compositions containing them.

Angiotensin II is known to be a circulatory hormone which can also act as a neuropeptide at the level of the central nervous system as indicated in particular in the European Patent Applications EP 0,465,368 and EP 0,503,162, or also International Patent Application WO 91/14367.

It has recently been shown that in fact two sub-types of angiotensin II receptors exist: the $AT_1$ receptor and the $AT_2$ receptor.

Research was initially centered on showing $AT_1$ receptor antagonists as substances with anti-hypertensive activity.

It has just been shown that the products of formula (I) of the present invention have an affinity not only for the $AT_1$ receptor but also for the $AT_2$ receptor.

The products of formula (I) of the present invention can thus quite particularly be the subject of a new use for the treatment of illnesses resulting from an abnormal stimulation of the $AT_1$ and $AT_2$ receptors of angiotensin II.

Therefore a subject of the present invention is the new use, for the preparation of pharmaceutical compositions intended for the treatment of illnesses resulting from an abnormal stimulation of the $AT_1$ and $AT_2$ receptors of angiotensin II, of products of formula (I):

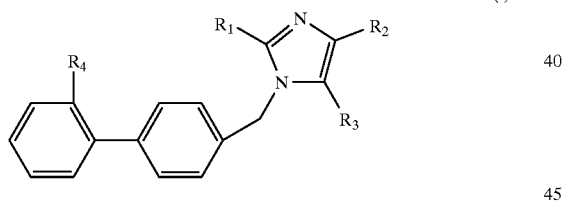

(I)

in which $R_1$ represents a linear or branched alkyl, alkylthio and alkoxy radical containing at most 6 carbon atoms, an aryl, arylthio or aryloxy radical, an arylalkyl radical in which the alkyl radical is linear or branched and contains at most 6 carbon atoms, $R_2$ represents:

a) the —S—R, —O—R and

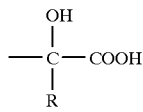

radicals in which

R represents a linear or branched alkyl or alkenyl radical containing at most 8 carbon atoms, a cycloalkyl radical containing at most 6 carbon atoms or an aryl radical, the alkyl, alkenyl, cycloalkyl and aryl radicals being optionally substituted by one or more radicals chosen from halogen atoms, the hydroxyl radical, linear or branched alkoxy and alkylthio radicals containing at most 6 carbon atoms and a phenyl radical itself optionally substituted by one or more radicals chosen from halogen atoms, the hydroxyl radical and linear or branched alkoxy radicals containing at most 6 carbon atoms, b) a halogen atom, c) a

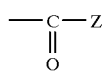

radical in which Z represents a hydroxyl, alkoxy or free, salified or esterified carboxy radical, $R_3$ is chosen from a free, salified or esterified carboxy radical, an acyl radical, optionally substituted by a phenyl, thienyl or tetrazolyl radical, a halogen atom, a linear or branched alkyl, alkenyl or alkylthio radical containing at most 8 carbon atoms, optionally substituted by one or more radicals chosen from halogen atoms, the following radicals:

hydroxyl, alkoxy, acyl, aryl, free, salified, esterified or amidified carboxy,

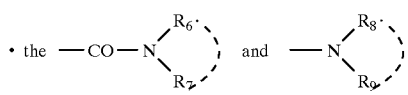

radicals in which:

either $R_6$ and $R_7$ or $R_8$ and $R_9$, identical or different, are chosen from:

the hydrogen atom, acyl, alkyl and alkenyl radicals containing at most 6 carbon atoms and alkylsulphonyl and arylsulphonyl radicals, the radicals being optionally substituted by one or more identical or different radicals chosen from halogen atoms, the hydroxyl radical, alkoxy radicals containing at most 6 carbon atoms or the free, salified or esterified carboxy radical, aryl, arylalkyl and arylalkenyl radicals, in which the linear or branched alkyl and alkenyl radicals contain at most 6 carbon atoms, these aryl, arylalkyl and arylalkenyl radicals being optionally substituted by one or more radicals chosen from halogen atoms, hydroxyl and nitro radicals, alkyl, alkenyl, haloalkyl, alkoxy and acyl radicals containing at most 6 carbon atoms, the amino radical optionally substituted by one or two identical or different alkyl radicals containing at most 6 carbon atoms and free, salified or esterified carboxy radicals, or on the one hand $R_6$ and $R_7$ and on the other hand $R_8$ and $R_9$ form respectively with the nitrogen atom to which they are linked a heterocyclic radical, chosen from the following radicals: imidazolyl, pyrrolyl, pyrrolinyl, pyrrolidinyl, piperidinyl, pyrimidinyl, pyridazinyl, piperazinyl, phenylpiperazinyl, oxazolyl, morpholinyl and thiomorpholinyl, azepine, indolyl, these radicals being optionally substituted by one or more identical or different radicals chosen from halogen atoms, hydroxyl, trifluoromethyl, alkyl and alkoxy radicals, these radicals containing at most 6 carbon atoms, or $R_8$ and $R_9$, identical or different, represent an amino acid or one of $R_8$ or $R_9$ represents a carbamoyl, alkoxycarbonyl or benzyloxycarbonyl radical or $R_8$ and $R_9$ form together with the nitrogen atom to which they are linked a phthalimido or succinimido radical, $R_4$ represents a) the following radicals: $—(CH_2)_{m1}—COOR_{14}$, $—(CH_2)_{m1}—CONHR_{14}$, $—(CH_2)_{m1}—CN$, in which m1 represents an integer from 0 to 4, $—SO_2—NH—SO_2—R_{14}$, $—NH—SO_2—R_{14}$, $—PO_3R_{14}$, $—NH—SO_2—CF_3$ and $R_{14}$ $—SO_2—N=C—N(CH_3)_2$, $—(CH_2)_{m1}—SO_3R_{14}$, $—CO—NH—OR_{14}$, $—CO—NH—NH—SO_2—CF_3$, $—CO—NH—SO_2—R_{14}$, $—CH_2SO_2NHCO—R_{14}$, $—CH_2—SO_2—NHR_{14}$, $—CH_2CONH—SO_2R_{14}$, $—NHSO_2NHCO—R_{14}$, $—NHCONHSO_2—R_{14}$, $NH—CH_2—SO_2—NHR_{14}$, $—CONHSO_2NR_{14}R_{15}$, $—SO_2NHCONR_{14}R_{15}$, $—SO_2N(R_{14})OR_{15}$, $—SO_2NHPO(R_{14})_2$, $—CONHPO(R_{14})_2$, $—SO_2NHCN$, $—SO_2NHCOR_{14}$, $SO_2—NHCO_2R_{14}$, $—SO_2NHSO_2NR_{14}R_{15}$, $—SO_2NHSO_2N(—CH_2—CH_2—)_2D$, $—NHSO_2NHSO_2R_{14}$, $—NHSO_2NHPO(R_{14})_2$, $—NR_{14}COCO_2H$, $—SO_2NHCO_2R_{14}$, $—SO_2—NH—CS—R_{14}$, $—SO_2—NH—CS—NH—R_{14}$, with D representing an oxygen or sulphur atom, b) the $—SO_2—W—R_{14}$ radical in which W represents the $—NR_{15}—$, $—NH—CO—$, $—NH—CO—O—$, $—N=CH—N—R_{15}$ or $—NH—CO—NR_{15}—$ radical, in which radical either $R_{14}$ and $R_{15}$, identical or different, are chosen from the hydrogen atom, the linear or branched alkyl or alkenyl radical containing at most 8 carbon atoms, the cycloalkyl radical containing at most 6 carbon atoms and the aryl radical, the alkyl, alkenyl, cycloalkyl and aryl radicals being optionally substituted by one or more radicals chosen from halogen atoms, the following radicals: hydroxyl, alkoxy containing at most 4 carbon atoms, nitro, cyano, amino, mono and dialkylamino, free, salified or esterified carboxy, haloalkyl, alkylthio, haloalkylthio, haloalkoxy, carbamoyl, acyl, acyloxy, cycloalkyl, cycloalkenyl, aryl, phenylthio, pyridyl, tetrazolyl, thienyl, nitropyridyl, pyrimidyl, diazolyl, piperidinyl, alkylpiperidinyl, thiazolyl, alkylthiazolyl, tetrahydrofuranyl and methyltetrahydrofuranyl optionally substituted by one or more radicals chosen from halogen atoms and the hydroxyl or alkoxyl radical containing at most 4 carbon atoms; or $R_{14}$ and $R_{15}$ form with the nitrogen atom to which they are linked a radical chosen from the following radicals: pyrrolyl, pyrrolinyl, pyrrolidinyl, piperazinyl, alkylpiperazinyl, phenylpiperazinyl, morpholinyl and indolinyl, it being understood that the alkyl radicals in the products of formula (I) are optionally interrupted by one or more heteroatoms chosen from oxygen, sulphur and nitrogen atoms and the sulphur atoms in the products of formula (I) can be optionally oxidized in the form of the sulphone or sulphoxide, said products of formula (I) being in all the possible racemic, enantiomeric and diastereoisomeric isomer forms as well as the addition salts with mineral and organic acids or with mineral and organic bases of said products of formula (I).

The products of formula (I) as defined above are described in the European Patent Applications EP 465368 and EP 503162 and can therefore be prepared in particular as is indicated in these European Patent Applications.

In the products of formula (I) and in what follows:

the term linear or branched alkyl radical preferably designates the following radicals: methyl, ethyl, propyl, isopropyl, butyl, isobutyl, sec-butyl and tert-butyl but can also represent a pentyl or hexyl radical and particularly isopentyl and isohexyl, the term linear or branched alkenyl radical preferably designates one of the following radicals: vinyl, allyl, 1-propenyl, butenyl and particularly 1-butenyl, or pentenyl, the term linear or branched alkynyl preferably designates an ethynyl, propargyl, butynyl or pentynyl radical.

Among the alkyl radicals interrupted by one or more heteroatoms, there can be mentioned for example the following radicals: methoxymethyl, methoxyethoxymethyl, propylthiopropyl, propyloxypropyl, propylthioethyl, methylthiomethyl, the term halogen atom preferably designates the chlorine atom, but can also represent a fluorine, bromine or iodine atom, the term linear or branched alkoxy radical preferably designates methoxy, ethoxy, propoxy or isopropoxy radicals, but can also represent a linear, secondary or tertiary butoxy radical, the term acyl radical preferably designates a radical having 1 to 6 carbon atoms such as for example the formyl, acetyl, propionyl, butyryl or benzoyl radical, but also the pentanoyl, hexanoyl, acryloyl, crotonoyl or carbamoyl radical, the term acyloxy radical designates for example a radical in which the acyl radical has the values indicated above and preferably designates a formyloxy, acetyloxy, propionyloxy, butyryloxy or benzoyloxy radical, the term cycloalkyl radical preferably designates the cyclopropyl, cyclobutyl radicals and quite particularly the cyclopentyl and cyclohexyl radicals, the term aryl radical designates the carbocyclic or heterocyclic, unsaturated monocyclic radicals or radicals constituted by condensed rings, it being understood that the heterocyclic radicals can contain one or more identical or different heteroatoms chosen from oxygen, nitrogen or sulphur atoms.

As examples of such an aryl radical, there can be mentioned the following radicals: phenyl, naphthyl, thienyl such as 2-thienyl and 3-thienyl, furyl such as 2-furyl, pyridyl such as 2-pyridyl and 3-pyridyl, pyrimidyl, pyrrolyl, thiazolyl, isothiazolyl, pyrazolyl, triazolyl, tetrazolyl, thiadiazolyl, thiatriazolyl, oxazolyl, oxadiazolyl, 3- or 4-isoxazolyl; benzothienyl such as 3-benzothienyl, benzofuryl, benzopyrrolyl, benzimidazolyl, benzoxazolyl, thionaphthyl, indolyl, indolinyl or purinyl, pyrrolidinyl, piperidino, morpholino, piperazinyl, these radicals being able to be substituted by one or more radicals as defined above such as for example in methylpiperazinyl, fluoromethylpiperazinyl, ethylpiperazinyl, propylpiperazinyl, phenylpiperazinyl or benzylpiperazinyl;

the term arylalkyl designates radicals in which the alkyl and aryl radicals respectively can take the values defined above for these radicals; as examples of such arylalkyl radicals there can be mentioned the following radicals: benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl or pyrrolylmethyl, it being understood that in the non-exhaustive list of examples of radicals as mentioned above, the alkyl radical can be represented just as equally by the ethyl, propyl or butyl radicals such as, for example, in the phenylethyl radical;

the term haloalkyl radical preferably designates the radicals in which the alkyl radical is as defined above and is substituted by one or more halogen atoms as defined above such as for example in bromoethyl, trifluoromethyl, trifluoroethyl or also pentafluoroethyl, the term alkylthio radical preferably designates the radicals in which the alkyl radical is as defined above such as for example in methylthio or ethylthio, the term haloalkylthio radical preferably designates the radicals in which the alkyl radical is as defined above and is substituted by one or more halogen atoms as defined above such as for example in bromoethylthio, trifluoromethylthio, trifluoroethylthio or also pentafluoroethylthio, the term haloalkoxy radical preferably designates the radicals in which the alkoxy radical is as defined above and is substituted by one or more halogen atoms as defined above such as for example in bromoethoxy, trifluoromethoxy, trifluoroethoxy or also pentafluoroethoxy, the term aryloxy radical preferably designates the radicals in which the aryl radical is as defined above such as for example in phenoxy, the term arylthio radical preferably designates the radicals in which the aryl radical represents the radicals as defined above such as for example in phenylthio, the term aryl radical substituted by an alkylthio radical represents for example the benzylthio or phenethylthio radical.

In all the radicals which can be represented by $R_1$, $R_2$, $R_3$ and $R_4$, as defined above, the sulphur atoms can be non-oxidized as in the alkylthio, arylthio radicals, and cycloalkylthio radicals such as for example cyclohexylthio or on the contrary be oxidized to give the alkylsulphinyl, cycloalkylsulphinyl, arylsulphinyl, alkylsulphonyl, cycloalkylsulphonyl or arylsulphonyl radicals:

the terms alkylthio, alkylsulphinyl and alkylsulphonyl radical designate radicals in which the linear or branched alkyl radical can represent, for example, the values indicated above for the alkyl radical; thus these radicals preferably represent methylthio, hydroxymethylthio, ethylthio, aminoethylthio, methylsulphinyl, ethylsulphinyl, methylsulphonyl, ethylsulphonyl radicals but can also represent a propylthio, isopropylthio, butylthio, sec-butylthio, tert-butylthio, isopentylthio or isohexylthio radical or those radicals in which the thio radical is oxidized into the sulphinyl or sulphonyl radical, the term arylthio, arylsulphinyl and arylsulphonyl radical designates the radicals in which the aryl radical can represent, for example, the values indicated above for the aryl radical such as, for example, in phenylthio, pyridylthio or pyrimidylthio, imidazolylthio, N-methylimidazolylthio or those radicals in which the thio radical is oxidized into the sulphinyl or sulphonyl radical such as for example in phenylsulphinyl or phenylsulphonyl.

Among the substituents of the alkylthio, alkoxy, arylthio and aryloxy radicals, optionally oxidized, there can be mentioned for example the hydroxyl, alkoxy, free, salified or esterified carboxy, acyl, acyloxy, alkyl or phenyl radicals, halogen atoms.

As examples of alkyl radicals substituted by an aryl radical, there can be mentioned, for example, the following radicals: benzyl, diphenylmethyl, triphenylmethyl, naphthylmethyl, indenylmethyl, thienylmethyl such as 2-thienyl methyl, furylmethyl such as furfuryl, pyridylmethyl, pyrimidylmethyl or pyrrolylmethyl, it being understood that in the non-exhaustive list of examples of radicals as mentioned above, the alkyl radical can be represented just as equally by the ethyl, propyl or butyl radicals such as, for example, in the phenethyl radical.

As examples of alkenyl radicals substituted by an aryl radical, there can be mentioned, for example, the examples given above of arylalkyl radicals in which the alkyl radical is replaced by an alkenyl radical such as for example in the phenylvinyl or phenylallyl radicals, it being understood that in these radicals the phenyl radical can be replaced just as equally by a naphthyl or pyridyl radical or also for example one of the aryl radicals as defined above.

The arylalkyl radicals as defined above preferably designate the alkylphenyl radicals such as benzyl, phenethyl, and also the phenylpropyl and phenylbutyl radicals.

The carbamoyl and amino radicals which can be represented or carried by one or more of the optional substituents of the radicals defined in the products of formula (I) and in what follows, designate radicals in which two radicals, identical or different, are linked to the nitrogen atom, and which are chosen from the following: the hydrogen atom to give the amino radical; the alkyl radicals as defined above to give the monoalkyl- or dialkylamino radicals in which the linear or branched alkyl radicals contain 1 to 6 carbon atoms; the phenyl, benzyl, phenethyl or naphthyl radicals, all these radicals being optionally substituted as indicated above and hereafter.

When $R_6$ and $R_7$ on the one hand, $R_8$ and $R_9$ on the other hand or $R_{14}$ and $R_{15}$ also on the other hand, as defined above, form, together with the nitrogen atom to which they are linked, a heterocycle, it is, for example, one of the following rings: pyrrolyl, imidazolyl, indolyl, indolinyl, purinyl, pyrrolidinyl, piperidino, morpholino, piperazinyl, imidazolidinyl, pyrazolidinyl, thiomorpholinyl, azepine; these radicals can be optionally substituted by the substituents already mentioned previously and especially by one or more radicals chosen from chlorine and fluorine atoms, the following radicals: methyl, ethyl, isopropyl, tert-butyl, methoxy, ethoxy, propoxy, benzoyl, methoxycarbonyl, ethoxycarbonyl, such as for example in methylpiperazinyl, ethylpiperazinyl, propylpiperazinyl, phenylpiperazinyl or benzylpiperazinyl: in these last two radicals, the phenyl and benzyl radicals can be substituted as indicated previously in the aryl, arylalkyl and arylalkenyl radicals, such as for example in chlorophenyl or trifluorophenyl.

The heterocycle which can be formed by $R_6$ and $R_7$ on the one hand, $R_8$ and $R_9$ on the other hand or $R_{14}$ and $R_{15}$ also on the other hand respectively with the nitrogen atom to which they are linked preferably represents a saturated heterocycle.

Moreover, in the products of formula (I), the carbamoyl or amino radicals are such that the radicals carried by the nitrogen atom, identical or different, can represent aliphatic or cyclized chains or can form with the nitrogen atom to which they are linked a heterocycle, as has been defined above for $R_6$, $R_7$, $R_8$, $R_9$, $R_{14}$ and $R_{15}$.

The substituted carbamoyl and substituted amino radicals designate respectively the radicals in which the nitrogen atom can be substituted by one or two radicals chosen from the radicals as defined previously, in particular the alkyl radical or radicals chosen from the alkyl radicals as defined above as for example for monoalkylamino in methylamino or ethylamino or isopropylamino or for example for dialkylamino in dimethylamino, diethylamino or also methylethylamino, these alkyl radicals being optionally substituted as indicated above, such as for example the methoxymethyl, methoxyethyl, ethoxyethyl radicals.

By way of example and in a non-exhaustive manner, the term carbamoyl radical designates carbamoyl radicals substituted on the nitrogen atom by one or two optionally substituted alkyl radicals as defined above, to form in particular an N-monoalkyl carbamoyl group such as N-methylcarbamoyl, N-ethylcarbamoyl or an N,N-dialkyl carbamoyl group, such as N,N-dimethylcarbamoyl, N,N-diethylcarbamoyl; an N-(hydroxyalkyl)carbamoyl group, such as N-(hydroxymethyl)carbamoyl, N-(hydroxyethyl) carbamoyl, phenylcarbamoyl; pyridylcarbamoyl; benzylcarbamoyl; N-methyl N-phenylcarbamoyl; pyridylmethylcarbamoyl. Furthermore, among the substituted alkyl radicals, there can also be mentioned the alkyl radicals substituted by a carbamoyl radical as defined above, to form a carbamoylalkyl group such as carbamoylmethyl or carbamoylethyl.

The amino radical can be an alkoxycarbonylamino radical, this radical then preferably being the tert-butyloxycarbonylamino radical or the benzyloxycarbonylamino radical.

The amino and carbamoyl radicals can also in particular be substituted by one or two amino acids chosen from the 20 natural amino acids such as in particular proline or for example glycine, alanine, leucine, isoleucine, valine or phenylalanine or one of the other natural amino acids known to a man skilled in the art.

According to whether m1 represents the value 0, 1, 2, 3 or 4, the —(CH$_2$)$_m$— radical represents a single bond, the methylene radical, the ethylene, propylene, isopropylene or butylene radical.

The carboxy radical or radicals of the products of formula (I) can be salified or esterified by the various groups known to a man skilled in the art amongst which there can be mentioned, for example:

amongst the salification compounds, mineral bases such as, for example, an equivalent of sodium, potassium, lithium, calcium, magnesium or ammonium or organic bases such as, for example, methylamine, propylamine, trimethylamine, diethylamine, triethylamine, N,N-dimethylethanolamine, tris (hydroxymethyl)amino methane, ethanolamine, pyridine, picoline, dicyclohexylamine, morpholine, benzylamine, procaine, lysine, arginine, histidine, N-methylglucamine, amongst the esterification compounds, alkyl radicals in order to form alkoxy carbonyl groups such as, for example, methoxycarbonyl, ethoxycarbonyl, tert-butoxycarbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic and aryldisulphonic.

When R$_2$ and R$_3$ both represent a sulphurous group, R$_2$ and R$_3$ being identical or different, in the preferred products of the invention these sulphurous groups do not necessarily have the same oxidation number.

R$_2$ and R$_3$ can thus in particular represent alkylthio radicals, substituted by one or more halogen atoms such as chlorine and fluorine, in order to give for example the following radicals: —S—CF$_3$; —S—CHF$_2$; —S—CH$_2$F; —S—CF$_2$—CHF$_2$; —S—CF$_2$—CF$_3$.

A particular subject of the invention is the use as defined above of the products of formula (I) as defined above and corresponding to formula (I$_A$):

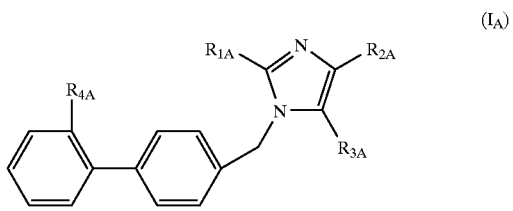

in which R$_{1A}$ represents a linear or branched alkyl or alkylthio radical, containing at most 6 carbon atoms, R$_{2A}$ represents
a) the —S—R$_A$ and

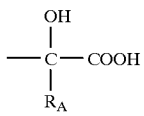

radicals in which R$_A$ represents a linear or branched alkyl or alkenyl radical, containing at most 8 carbon atoms, a cycloalkyl or phenyl radical, these radicals being optionally substituted by one or more radicals chosen from halogen atoms and more particularly fluorine,
b) a halogen atom,
c) a

radical in which Z represents a free, salified or esterified carboxy radical.

R$_{3A}$ represents
a free, salified, esterified or amidified carboxy radical,
a formyl and acetyl radical optionally substituted by a phenyl, benzyl, phenethyl or tetrazolyl radical,
a halogen atom,
a linear or branched alkyl, alkenyl or alkylthio radical, containing at most 8 carbon atoms, optionally substituted by one or more radicals chosen from the following radicals: hydroxyl, alkoxy, acyl, phenyl, free, salified, esterified or amidified carboxy, carbamoyl and amino optionally substituted on the nitrogen atom by one or two radicals chosen from the following radicals: alkyl containing at most 6 carbon atoms, acyl, alkylsulphonyl, phenylsulphonyl, phenyl, phenylalkyl, these radicals being optionally substituted by one or more radicals chosen from halogen atoms, the hydroxyl radical and linear or branched alkoxy radicals containing at most 4 carbon atoms, $R_{4A}$ represents $SO_2$—$W_A$—$R_{16A}$, in which $W_A$ represents the —NH—, NH—CO—, —NH—CO—O—,

or —NH—CO—NH— radical and $R_{16A}$ and $R_{17A}$ represent a hydrogen atom, a linear or branched alkyl or alkenyl radical containing at most 4 carbon atoms, or an aryl radical, these radicals being optionally substituted by one or more radicals chosen from halogen atoms, the following radicals: hydroxyl or alkoxy containing at most 4 carbon atoms, nitro, cyano, amino, mono- and dialkylamino, free, salified or esterified carboxy, cyclohexyl, cyclohexenyl, pyridyl, thienyl and phenyl, these radicals being optionally substituted by a halogen atom or a hydroxyl or alkoxy radical containing at most 4 carbon atoms, it being understood that the sulphur atoms in the products of formula ($I_A$) can optionally be oxidized in the form of the sulphone or sulphoxide, said products of formula ($I_A$) being in all the possible racemic, enantiomeric and diastereoisomeric isomer forms as well as the addition salts with mineral and organic acids or with mineral and organic bases of said products of formula ($I_A$).

The $SO_2$—$WA$—$R_{16A}$ radical which is represented by $R_{4A}$ can in particular represent the following radicals:

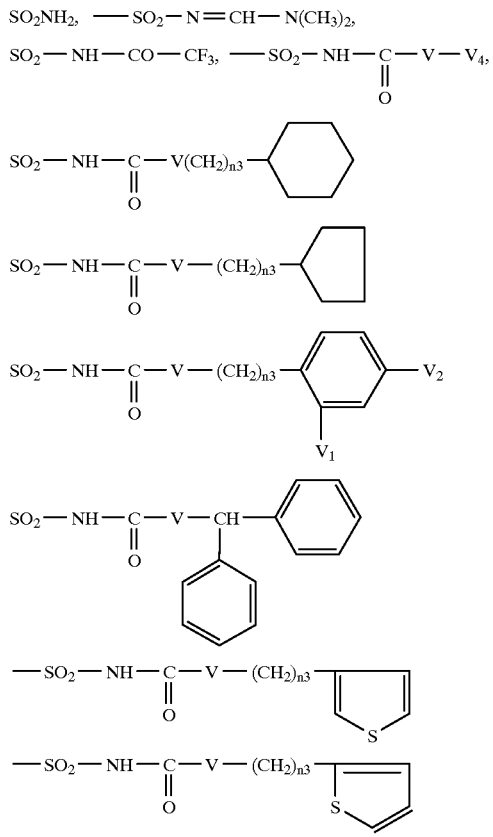

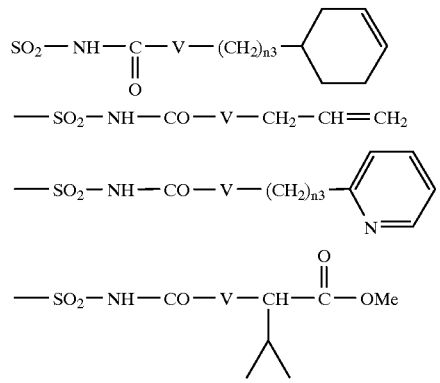

with n3 representing an integer from 0 to 3, V represents —NH—, —O— or a single bond, $V_1$ and $V_2$, identical or different, represent a hydrogen atom, a halogen atom, in particular chlorine and fluorine and an alkoxy radical, in particular methoxy, $V_4$ represents a hydrogen atom, an alkyl radical such as in particular methyl, ethyl, propyl and butyl.

A particular subject of the invention is the use as defined above of the following products of formula (I), called P1 to P13 respectively:

2-butyl 1-[(2'-(((((cyclohexylmethyl)amino)carbonyl) amino)sulphonyl)(1,1'-biphenyl)4-yl)methyl]4-(methylthio)1H-imidazole 5-carboxylic acid, 2-butyl 4-(methylthio)1-[(2'-(((((phenylmethyl)amino) carbonyl)amino)sulphonyl)(1,1'-biphenyl)4-yl)methyl] 1H-imidazole 5-carboxylic acid, 2-butyl 4-(methylthio)1-[(2'-(((((1-beta-phenylpropyl) amino)carbonyl)amino)sulphonyl)( 1,1'-biphenyl)4-yl) methyl]1H-imidazole 5-carboxylic acid, 2-butyl 4-(methylthio)1-[(2'-(((((1-(4-phenylbutyl))amino) carbonyl)amino)sulphonyl)(1,1'-biphenyl)4-yl)methyl] 1H-imidazole 5-carboxylic acid, 2-butyl 1-[(2'-((((((4-methoxy)phenylmethyl)amino) carbonyl)amino)sulphonyl)(1,1'-biphenyl)4-yl)methyl]4-methylthio 1H-imidazole 5-carboxylic acid, 2-butyl 1-[(2'-((((((4-fluoro)phenylmethyl)amino)carbonyl) amino)sulphonyl)(1,1'-biphenyl)4-yl)methyl]4-methylthio 1H-imidazole 5-carboxylic acid, 2-butyl 1-[(2'-(((((1-(1-carboxy 2-phenyl)ethyl)amino) carbonyl)amino)sulphonyl)(1,1'-biphenyl)4-yl)methyl]4-methylthio 1H-imidazole 5-carboxylic acid, 2-butyl 4-(methylthio)1-[(2'-((((2-thienyl) methoxycarbonyl)amino)sulphonyl)(1,1'-biphenyl)4-yl) methyl]1H-imidazole 5-carboxylic acid, 2-butyl 4-(methylthio)1-[(2'-((((3-thienyl) methoxycarbonyl)amino)sulphonyl)(1,1'-biphenyl)4-yl) methyl]1H-imidazole 5-carboxylic acid, 2-butyl 1-[(2'-((((cyclohexen 4-yl)methoxycarbonyl)amino) sulphonyl)(1,1'-biphenyl)4-yl)methyl]4-methylthio 1H-imidazole 5-carboxylic acid, 2-butyl 1-[(2'-((((cyclohexyl)methoxycarbonyl)amino) sulphonyl)(1,1'-biphenyl)4-yl)methyl]4-methylthio 1H-imidazole 5-carboxylic acid, 2-butyl 4-(methylthio)1-[(2'-(((phenylmethoxycarbonyl) amino)sulphonyl)(1,1'-biphenyl)4-yl)methyl]1H-imidazole 5-carboxylic acid, (phenylmethyl)((4'-((2-butyl 5-formyl 4-methoxy 1H-imidazol 1-yl)methyl)(1,1'-biphenyl)2-yl)sulphonyl) carbamate.

The products indicated above can in particular be prepared as indicated in the European Patent Application EP 0503162.

Among the products of formulae (I) and (I$_A$), certain products of formula (I$_B$) are new.

A particular subject of the invention is also the products of formula (I$_B$):

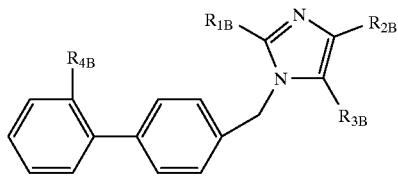
(I$_B$)

in which

R$_{1B}$ represents a linear or branched alkyl radical containing at most 4 carbon atoms, R$_{2B}$ represents a linear or branched alkylthio radical containing at most 4 carbon atoms, optionally substituted by one or more fluorine atoms, R$_{3B}$ represents
  a free, salified, esterified or amidified carboxy radical, an acyl, carbamoyl radical,
  an alkyl and alkenyl radical containing at most 6 carbon atoms substituted by one or more radicals chosen from halogen atoms, the following radicals: hydroxyl, alkoxy, free, salified, esterified or amidified carboxy, phenyl and carbamoyl, optionally substituted by a phenyl or benzyl radical, R$_{4B}$ represents one of the following radicals: —SO$_2$—NH$_2$, —SO$_2$—N═CH—N(CH$_3$)$_2$,

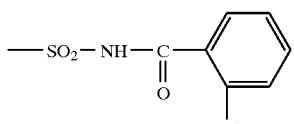

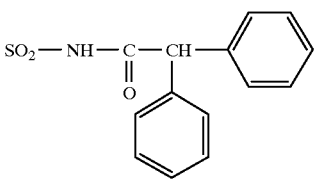

—SO$_2$—NH—CO$_2$Et, —SO$_2$—NH—CO$_2$Pr, —SO$_2$—NH—CO$_2$Bu, —SO$_2$—NH—CO$_2$H,

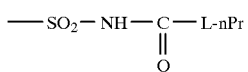

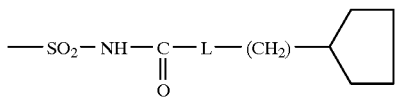

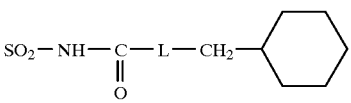

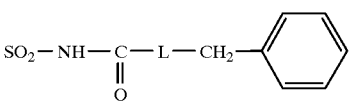

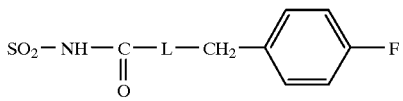

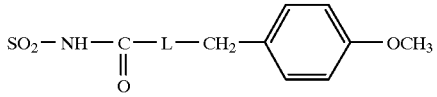

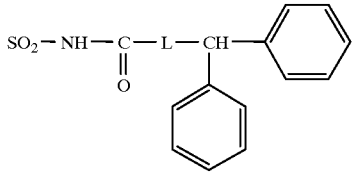

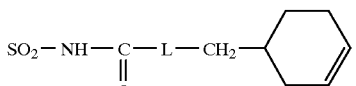

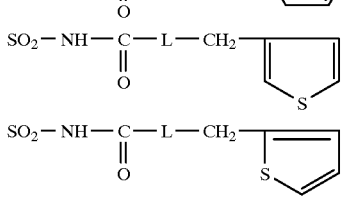

with L representing —O— or —NH—, it being understood that the sulphur atoms in the products of formula (I$_B$) can optionally be oxidized in the form of the sulphone or sulphoxide, said products of formula (I$_B$) being in all the possible racemic, enantiomeric and diastereoisomeric isomer forms, as well as the addition salts with mineral and organic acids or with mineral and organic bases of said products of formula (I$_B$).

A quite particular subject of the invention is the products of formula (I$_B$) as defined above, corresponding to the following formulae:

2-butyl alpha-hydroxy alpha-methyl 4-(methylthio)1-[(2'-(((((phenylmethoxy)carbonyl)amino)sulphonyl)(1,1'-biphenyl)4-yl)methyl]1H-imidazole 5-acetic acid, 2-butyl alpha-hydroxy alpha-methyl 4-(methylthio)1-[(2'-(((((propylamino)carbonyl)amino)sulphonyl)(1,1'-biphenyl)4-yl)methyl]1H-imidazole 5-acetic acid, 2-butyl alpha-hydroxy alpha-methyl 4-(methylthio)1-[(2'-(((((phenylmethyl)amino)carbonyl)amino)sulphonyl)(1,1'-biphenyl)4-yl)methyl]1H-imidazole 5-acetic acid, 2-butyl 1-[(2'-(((((cyclohexylmethyl)amino)carbonyl)amino)sulphonyl)(1,1'-biphenyl)4-yl)methyl]alpha-hydroxy alpha-methyl 4-(methylthio)1H-imidazole 5-acetic acid, 1-[(2'-(((((phenylmethyl)amino)sulphonyl)(1,1'-biphenyl)4-yl)methyl]alpha-hydroxy 4-(methylthio)2-propyl 1H-imidazole 5-acetic acid, sodium 1-[(2'-(((((cyclohexylmethyl)amino)carbonyl)amino)sulphonyl)(1,1'-biphenyl)4-yl)methyl]4-(methylthio)2-propyl 1H-imidazole 5-carboxylate, 4-(methylthio)1-[(2'-(((((phenylmethyl)amino)carbonyl)amino)sulphonyl)(1,1'-biphenyl)4-yl)methyl]2-propyl 1H-imidazole 5-carboxylic acid, sodium alpha-butyl alpha-hydroxy 4-(methylthio)1-[(2'-(((((phenylmethyl)amino)carbonyl)amino)sulphonyl)(1,1'-biphenyl) 4-yl)methyl]2-propyl 1H-imidazole 5-acetate, alpha-hydroxy 4-(methylthio)alpha-phenyl 1-((2'-(((((phenylmethyl)amino)carbonyl)amino)sulphonyl)(1,1'-biphenyl)4-yl)methyl)2-propyl 1H-imidazole 5-acetic acid, 1-((2'-(((((cyclohexylmethyl)amino)carbonyl)amino)
sulphonyl)(1,1'-biphenyl)4-yl)methyl)4-(difluoromethyl)
thio)2-propyl 1H-imidazole 5-carboxylic acid, 4-((difluoromethyl)thio)1-((2'-(((((phenylmethyl)amino)
carbonyl)amino)sulphonyl)1,1'-biphenyl)4-yl)methyl)2-
propyl 1H-imidazole 5-carboxylic acid, 4-((difluoromethyl)thio)2-propyl 1-((2'-(((((2-
thienylmethyl)amino)carbonyl)amino)sulphonyl)(1,1'-
biphenyl)4-yl)methyl)1H-imidazole 5-carboxylic acid.

Also a subject of the invention is a preparation process for the products of formula (I), as defined above, characterized in that:

either a compound of formula (II):

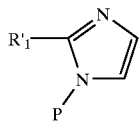

(II)

in which $R'_1$ has the meaning indicated above for $R_1$, in which the optional reactive functions are optionally protected by protective groups and P represents a protective group of the nitrogen atom, is subjected to a halogenation reaction in order to obtain a compound of formula (III):

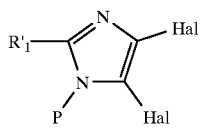

(III)

in which $R'_1$ and P have the meanings indicated above and Hal represents a halogen atom, which is subjected to a halogen-metal exchange reaction on one of the halogen atoms then to a reaction with a compound of formula $(IV_a)$, $(IV_b)$, $(IV_c)$, $(IV_d)$ or $(IV_e)$:

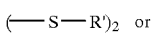  (IV$_a$)

  (IV$_b$)

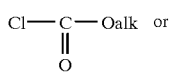  (IV$_c$)

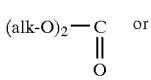  (IV$_d$)

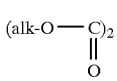  (IV$_e$)

in which R' has the meaning indicated above for R, in which the optional reactive functions are optionally protected by protective groups, and alk represents an alkyl radical containing at most 4 carbon atoms, in order to obtain the compound of formula (V):

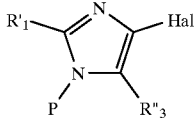

(V)

in which $R'_1$, P and Hal have the meanings indicated above and $R''_3$ represents S—R' or K—O-alk as defined above with K representing the

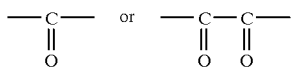

radical, which compound of formula (V) can be subjected to a halogen-metal exchange reaction on the halogen atom then to a reaction with a compound of formula $(IV'_a)$, $(IV'_b)$, $(IV'_c)$, $(IV'_d)$ or $(IV'_e)$:

(—S—R")$_2$     (IV'$_a$)

or

MeSO$_2$SR"     (IV'$_b$)

     (IV'$_c$)

     (IV'$_d$)

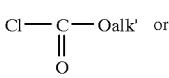     (IV'$_e$)

in which R", identical to or different from R', has the meaning indicated above for R, in which the optional reactive functions are optionally protected by protective groups and alk', identical to or different from alk, represents an alkyl radical containing at most 4 carbon atoms, in order to obtain the compound of formula (VII):

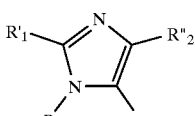

(VII)

in which $R'_1$ and P have the meanings indicated above, and $R''_2$ and $R''_3$, identical or different, represent —S—R', —S—R", —K—Oalk or —K—Oalk' as defined above in which R', R", alk, alk' and K have the meanings indicated above, from which product of formula (VII) the amine function blocked by P as defined above is released, followed by reaction with a compound of formula (VIII):

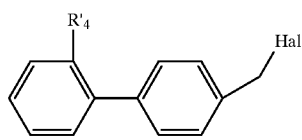
(VIII)

in which R'₄ has the meaning indicated above for R₄, in which the optional reactive functions are optionally protected by protective groups and Hal represents a halogen atom in order to obtain a product of formula (I₁):

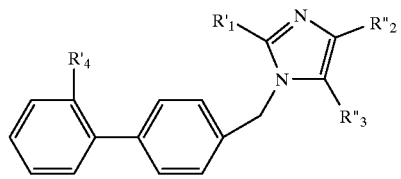
(I₁)

in which R'₁, R"₂, R"₃ and R'₄ have the meanings indicated above, or a compound of formula (IX):

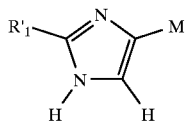
(IX)

in which R'₁ has the meaning indicated above and M represents a hydrogen atom or the R'₂ radical which has the meaning indicated above for R₂, in which the optional reactive functions are optionally protected by protective groups, is subjected to a reaction with the compound of formula (VIII) as defined above, in order to obtain a product of formula (X):

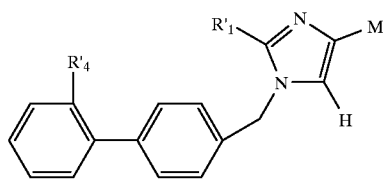
(X)

in which R'₁, M and R'₄ have the meanings indicated above, which products of formula (X), when M represents R'₂ as defined above, are subjected to a halogenation reaction in order to obtain the product of formula (XI):

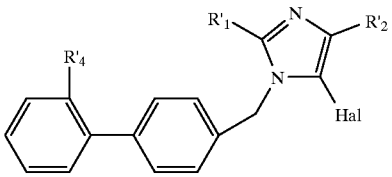
(XI)

in which R'₁, R'₂, R'₄ and Hal have the meanings indicated above, which is subjected to a halogen-metal exchange reaction then to a reaction with a compound of formula (XII):

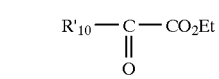
(XII)

in which R'₁₀ has the meaning indicated above for R₁₀, in which the optional reactive functions are optionally protected by protective groups, in order to obtain a product of formula (I₂):

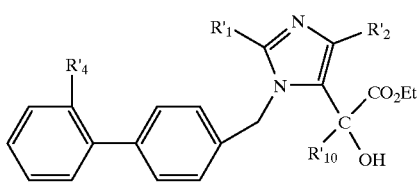
(I₂)

in which R'₁, R'₂, R'₄ and R'₁₀ have the meanings indicated above, either the product of formula (I₂) is subjected to a saponification reaction in order to obtain the product of formula (I₄):

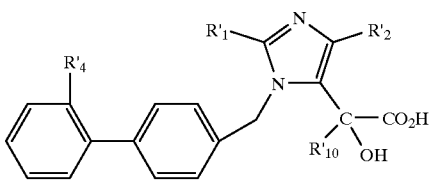
(I₄)

in which R'₁, R'₂, R'₄ and R'₁₀ have the meanings indicated above, which product of formula (X), when M represents a hydrogen atom, can be subjected to a halogenation reaction in order to obtain the product of formula (XIV):

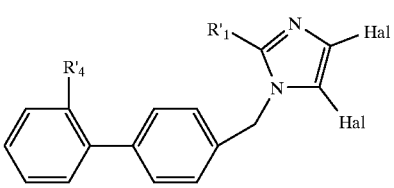
(XIV)

in which R'₁, R'₄ and Hal have the meanings indicated above, which can be subjected to a halogen-metal exchange reaction then to the action of a compound of formula (IV$_a$), (IV$_b$), (IV$_c$), (IV$_d$) or (IV$_e$) as defined above in order to obtain the product of formula (I$_7$):

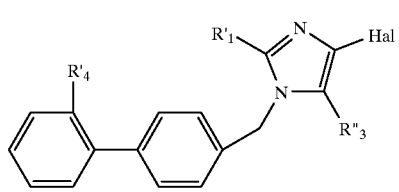

(I$_7$)

in which R'$_1$, R'$_4$, Hal and R"$_3$ have the meanings indicated above, which product of formula (I$_7$) can be subjected to a halogen-metal exchange reaction then to the action of a compound of formula (IV'$_a$), (IV'$_b$), (IV'$_c$), (IV'$_d$) or (IV'$_e$), as defined above, in order to obtain a product of formula (I$_8$):

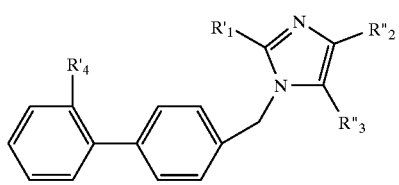

(I$_8$)

in which R'$_1$, R'$_4$, R"$_2$ and R"$_3$ have the meanings indicated above,
or a compound of formula (XX):

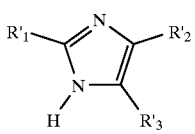

(XX)

in which R'$_1$ and R'$_2$ have the meanings indicated above and R'$_3$ has the meaning indicated above for R$_3$ in which the optional reactive functions are optionally protected by protective groups, is subjected to a reaction with the compound of formula (VIII) as defined above, in order to obtain a product of formula (I'):

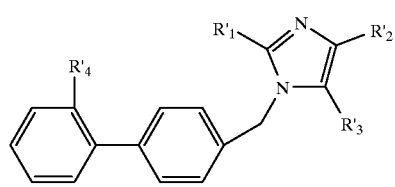

(I')

in which R'$_1$, R'$_2$, R'$_3$ and R'$_4$ have the meanings indicated above,
which products of formulae (I$_1$), (I$_2$), (I$_3$), (I$_4$), (I$_5$), (I$_6$), (I$_7$), (I$_8$) and (I') can be products of formula (I) and which, in order to obtain these or other products of formula (I), can be subjected, if desired and if necessary, to one or more of the following conversion reactions, in any order:

a) esterification of the acid function,
b) saponification of the ester function into an acid function,
c) conversion of the ester function into an acyl function,
d) conversion of the cyano function into an acid function,
e) conversion of the acid function into an amide function, then optionally into a thioamide function,
f) reduction of the carboxy function to an alcohol function,
g) conversion of the alkoxy function into a hydroxyl function, or also of the hydroxyl function into an alkoxy function,
h) oxidation of the alcohol function into an aldehyde, acid or ketone function,
i) conversion of the formyl radical into the carbamoyl radical,
j) conversion of the carbamoyl radical into the nitrile radical,
k) conversion of the nitrile radical into tetrazolyl,
l) oxidation of the alkylthio or arylthio group into the corresponding sulphoxide or sulphone,
m) conversion of the sulphide, sulphoxide or sulphone function into a corresponding sulphoximine function,
n) conversion of the oxo function into a thioxo function,
o) dehydration of a hydroxylalkyl radical to an alkenyl radical,
p) conversion of an acid function into the following function

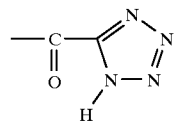

q) conversion of the beta-keto-sulphoxide function into an alpha-keto thio ester function,
r) conversion of a carbamate into urea and in particular of a sulphonylcarbamate into sulphonylurea,
s) elimination of the protective groups which can be carried by the protected reactive functions,
t) salification by a mineral or organic acid or by a base in order to obtain the corresponding salt,
u) resolution of the racemic forms into resolved products, said products of formula (I) thus obtained being in all the possible racemic, enantiomeric and diastereoisomeric isomer forms.

Under preferential conditions for implementing the invention, the halogenation reaction of the compounds of formulae (II) and (X) as defined above into compounds of formula (III) and (XI) or (XIV) as defined above respectively, can be carried out under the usual conditions known to a man skilled in the art and in particular by bromination using N-bromosuccinimide in dichloromethane or also bromine in acetic acid.

The corresponding compound of formula (V) can be obtained by the reaction of the compound of formula (III) as defined above with an organo-metallic compound such as n-butyllithium in a solvent such as tetrahydrofuran at a temperature of approximately −78° C. followed by the action of a compound of formula (IV$_a$), (IV$_b$), (IV$_c$), (IV$_d$) or (IV$_e$).

The reaction of the product of formula (V) as defined above with the compound of formula (IV'$_a$), (IV'$_b$), (IV'$_c$) (IV'$_d$) or (IV'$_e$), as defined above, in order to obtain a compound of formula (VII) as defined above, can be carried out in an identical manner using n-butyllithium as the metallation agent.

The amine function of the compound of formula (VII) as defined above, protected by P as defined above, can be released under the usual conditions known to a man skilled in the art and in particular when P represents the —CH$_2$—O—(CH$_2$)$_2$—Si(CH$_3$)$_3$ radical, by the action of trifluoroacetic acid or also in the presence of a fluoride ion.

In the product of formula (VIII), Hal preferably represents a bromine atom but can also represent a chlorine or iodine atom.

The reaction of the product of formula (VIII) on the product of formula (VII) or (IX) or (XX), can be carried out in a solvent such as for example dimethylformamide or also dimethylacetamide, tetrahydrofuran, dimethoxyethane or dimethylsulphoxide under reflux of the solvent or at ambient temperature, preferably under agitation; the reaction is preferably carried in the presence of a base such as for example sodium or potassium hydride or also sodium or potassium carbonate, sodium or potassium methylate or ethylate or tert-butylate.

The compound of formula (I$_2$) as defined above is obtained by the action, on the magnesium-compound derivative of the compound of formula (XI), of the compound of formula (XII) as defined above in a solvent such as for example tetrahydrofuran or toluene.

The magnesium-compound derivative of the compound of formula (XI) is obtained by the action of the compound of formula (XI) as defined above in which Hal can for example represent a bromine atom, with a magnesium compound such as for example isopropyl magnesium chloride, in a solvent such as for example toluene.

The saponification reaction of the product of formula (I$_2$) as defined above into a product of formula (I$_4$) as defined above, can be carried out according to the usual methods known to a man skilled in the art, such as for example in the presence of soda or potash or also caesium carbonate, in a solvent such as methanol or ethanol, dioxane or dimethoxyethane.

The conversion reaction of the product of formula (XIV) as defined above, into the product of formula (I$_7$) as defined above then into the product of formula (I$_8$), as defined above, can be carried out under the same conditions as those defined for obtaining the products of formulae (V) and (VII) as defined above, starting from the product of formula (III) as defined above.

According to the values of R'$_1$, R'$_2$, R"$_2$, R'$_3$, R"$_3$ and R'$_4$, the products of formulae (I$_1$), (I$_2$), (I$_4$), (I$_7$), (I$_8$) and (I') constitute or do not constitute products of formula (I) and can produce products of formula (I), or be converted into other products of formula (I) by being subjected to one or more of reactions a) to u) indicated above.

Thus the various reactive functions which can be carried by certain compounds of the reactions defined above can, if necessary, be protected: they can be for example hydroxyl, acyl, free carboxy or also amino and monoalkylamino radicals which can be protected by the appropriate protective groups.

The following non-exhaustive list of examples of the protection of the reactive functions can be mentioned:
the hydroxyl groups can be protected for example by alkyl radicals such as tert-butyl, trimethylsilyl, tert-butyldimethylsilyl, methoxymethyl, tetrahydropyranyl, benzyl or acetyl,
the amino groups can be protected for example by the acetyl, trityl, benzyl, tert-butoxycarbonyl, phthalimido radicals or other radicals known in the chemistry of the peptides,
the acyl groups such as the formyl group can be protected for example in the form of cyclic or non-cyclic ketals or thioketals such as dimethyl- or diethylketal or ethylene dioxyketal, or diethylthioketal or ethylenedithioketal,
the acid functions of the products described above can be, if desired, amidified by a primary or secondary amine for example in methylene chloride in the presence, for example, of 1-ethyl-3-(dimethylaminopropyl) carbodiimide hydrochloride at ambient temperature:
the acid functions can be protected for example in the form of esters formed with easily cleavable esters such as benzyl or ter butyl esters or esters known in the chemistry of the peptides.

The reactions to which the products of formulae (I$_1$), (I$_2$), (I$_4$), (I$_7$), (I$_8$) and (I'), as defined above, can be subjected, if desired or if necessary, can be achieved, for example, as indicated hereafter.

a) The products described above can, if desired, be subjected to, on the optional carboxy functions, esterification reactions which can be carried out according to the usual methods known to a man skilled in the art.

b) The optional conversions of ester functions into an acid function of the products described above can, if desired, be carried out under the usual conditions known to a man skilled in the art, in particular by alkaline or acid hydrolysis for example using soda or potash in an alcoholic medium such as, for example, in methanol or also using sulphuric or hydrochloric acid.

c) The addition reaction on the

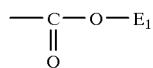

ester function in which E$_1$ can represent an alkyl or aryl radical optionally substituted and optionally protected in the form of a

acyl function can be achieved in particular by the action of the carbonated anion

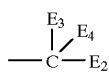

in which E$_2$, E$_3$ and E$_4$, identical or different, are chosen from the hydrogen atom, the following radicals: alkyl, alkylthioaryl, alkylsulphoxide, arylsulphoxide, alkylsulphone, arylsulphone, acyl, free, salified, esterified or amidified carboxy, the alkyl, alkylthio and aryl radicals being optionally substituted and optionally protected as indicated above.

Such a reaction is carried out in particular as described in the experimental part, or according to the usual methods known to a man skilled in the art.

d) The optional cyano functions of the products described above can, if desired, be converted into an acid function under the usual conditions known to a man skilled in the art, for example by double hydrolysis carried out in an acid medium such as for example in a mixture of sulphuric acid, glacial acetic acid and water, these three compounds preferably being in equal proportions, or also in a mixture of soda, ethanol and water under reflux.

e) The conversion reaction of the acid function into an amide function can in particular be carried out by the formation, first of all, of an acid chloride according to the usual conditions known to a man skilled in the art and for example by the action of SOCl$_2$ then amidification as indicated above, or also by direct amidification of the above acid.

In particular, the following radical can be obtained

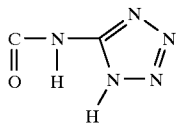

by converting the acid function into an acid chloride, in particular by the action of SOCl$_2$ in a solvent such as for example toluene, or benzene, then by reacting the amine

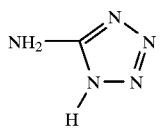

The amide thus obtained can then if desired, be converted into the thioamide by the action in particular of LAWESSON reagent in toluene.

f) The optional free or esterified carboxy functions of the products described above can, if desired, be reduced into an alcohol function by methods known to a man skilled in the art: the optional esterified carboxy functions can, if desired, be reduced to an alcohol function by methods known to a man skilled in the art and in particular by lithium-aluminium hydride in a solvent such as for example tetrahydrofuran or also dioxane or ethyl ether.

The optional free carboxy functions of the products described above can, if desired, be reduced to an alcohol function in particular by boron hydride.

g) The optional alkoxy functions such as in particular methoxy of the products described above can, if desired, be converted into a hydroxyl function under the usual conditions known to a man skilled in the art for example by boron tribromide in a solvent such as for example methylene chloride, by pyridine hydrobromide or hydrochloride or also by hydrobromic or hydrochloric acid in water or trifluoro-acetic acid under reflux.

h) The optional alcohol functions of the products described above can, if desired, be converted into an aldehyde or acid function by oxidation under the usual conditions known to a man skilled in the art such as for example by the action of manganese oxide in order to obtain the aldehydes or Jones reagent in order to obtain the acids.

i) j) The conversion reactions of the formyl radical into a carbamoyl radical and of the carbamoyl radical into a nitrile radical are carried out in particular for R$_3$ and R$_4$ according to the usual conditions known to a man skilled in the art, such as for example passage via the keto nitrile and displacement by an amine (Chem. Comm. 1971, p. 733).

k) The optional nitrile functions of the products described above can, if desired, be converted into tetrazolyl under the usual conditions known to a man skilled in the art such as for example by the cycloaddition of a metallic azide such as for example sodium azide or a trialkyltin azide on the nitrile function as indicated in the method described in the article referenced as follows: J. Organometallic Chemistry., 33, 337 (1971) KOZIMA S. & coll.

l) The optional alkylthio or arylthio groups of the products described above can, if desired, be converted into the corresponding sulphoxide or sulphone functions under the usual conditions known to a man skilled in the art such as for example by peracids such as for example peracetic acid or metachloroperbenzoicacid or also by ozone, oxone, sodium periodate in a solvent such as for example methylene chloride or dioxane at ambient temperature.

Obtaining the sulphoxide function can be encouraged by an equimolar mixture of the product containing an alkylthio or arylthio group and the reagent such as in particular a peracid.

Obtaining the sulphone function can be encouraged by a mixture of the product containing an alkylthio or arylthio group with an excess of the reagent such as in particular a peracid.

m) The optional sulphide, sulphoxide or sulphone functions of the products described above can, if desired, be converted into the corresponding sulphoximine functions under the usual conditions known to a man skilled in the art: non-exhaustive examples of the preparation of products containing a sulphoximine function are described below.

Thus for example for the preparation of compounds such as N-(arylsulphonyl)sulphoximines and for example in the case where the aryl group is a toluene radical, the sulphoximine can be obtained by the action of paratoluenesulphonyl nitride on the corresponding sulphoxide, i.e. —S(O)CH$_3$, preferably in the presence of copper as indicated, for example, in the following reference:

J. A. C. S., 95, pp. 4287 (1973) JOHNSON C.R. & coll.

Another method also used consists of treating N-tosylsulphilimine, itself prepared from the sulphide, by the action, for example, of chloramine "T", by an oxidizing agent such as, for example, sodium hypochlorite under phase transfer conditions as indicated, for example, in the following reference:

J. Org. Chem., 49, pp. 2282 (1984) AKUTAGAWA K. et al.

n) the conversion reaction of the oxo function into a thioxo function can be carried out in particular by LAWESSON reagent under the conditions defined above.

o) The dehydration reaction of a hydroxylalkyl radical into an alkenyl radical can in particular be carried out by means of an acid such as concentrated hydrochloric acid or sulphuric acid in an alcohol or dioxane.

p) The conversion reaction of the acid function into a tetrazolylcarboxy function can be carried out for example by preliminary conversion of the acid function into an acid chloride as indicated above, then by the action of cuprous cyanide, according to the usual conditions known to a man skilled in the art, on the acid chloride thus obtained, and in this way the

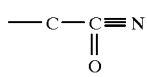

radical is obtained which can be converted into a

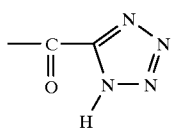

radical for example by the action of the compound Sn(Bu)$_3$N$_3$ in toluene, q) the conversion reaction of the beta keto sulphoxide function into an alpha keto thioester function can be carried out by bromination in the alpha position of the ketosulphoxide for example by the action of N-bromo-succinimide in for example methylene chloride then by a PUMMERER reaction carried out in a mixture of trifluoroacetic acid and methylene chloride or also a sulphuric acid and dioxane mixture.

In particular, as is defined above in c) and q), the following reaction diagram can be implemented:

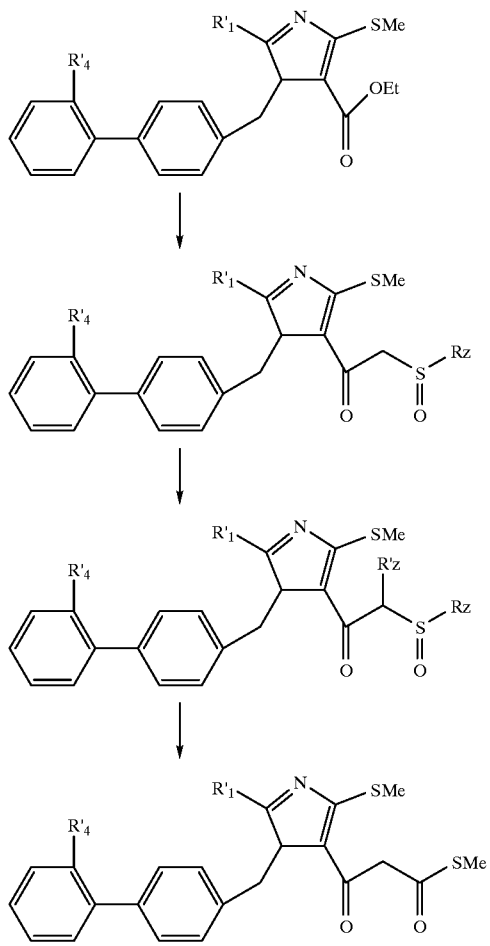

in which compounds R'$_1$ and R'$_4$ have the meanings indicated above, and Rz and R'z, identical or different, represent an alkyl or aryl radical optionally substituted as indicated above.

An illustration of this reaction diagram is given hereafter in the experimental part in Preparation 4.

r) The conversion reaction of a carbamate into urea and in particular of a sulphonylcarbamate into sulphonylurea, can be carried out for example under reflux of a solvent such as for example toluene in the presence of a suitable amine.

s) The elimination of the protective groups such as for example those indicated above can be carried out under the usual conditions known to a man skilled in the art, in particular by acid hydrolysis carried out with an acid such as hydrochloric, benzene sulphonic or paratoluene sulphonic, formic or trifluoroacetic acid or also by catalytic hydrogenation. The phthalimido group can be eliminated by hydrazine.

A list of different protective groups which can be used will be found for example in the Patent BF 2,499,995.

t) The products described above can, if desired, be subjected to salification reactions for example by a mineral or organic acid or by a mineral or organic base according to the usual methods known to a man skilled in the art.

u) The optional optically active forms of the products described above can be prepared by resolution of the racemics according to the usual methods known to a man skilled in the art.

Illustrations of such reactions defined above are given in the preparation of the examples described hereafter.

Certain starting products of formulae (II), (IX) and (XX) are known and can be prepared for example as indicated in the European Patent EP 168,950.

Other starting products of formulae (II), (IX) and (XX) can in particular be prepared as indicated in the European Patent EP 0,465,368 or in Preparations 1 to 5 described hereafter.

Certain starting products of formulae (II), (IX) and (XX) are commercially available such as for example: the following products of formula (II):
2-phenylimidazole
2-methoxymethylimidazole
2-propylimidazole
2-isopropylimidazole
2-ethylimidazole
2-methylimidazole
the following products of formula (IX):
4-methyl 2-phenylimidazole
2,4-dimethylimidazole
2-ethyl 4-methylimidazole.

Examples of commercially-available products of formula (XX) are given in Patent EP 0,465,368 or EP 0,503,162.

Certain products of formulae (II), (IX) and (XX) can also be prepared starting from other products of formula (II) or (IX) for example by subjecting them to one or more of the reactions described in points a) to u) above achieved as indicated above.

Certain products of formulae (IX) and (XX) can also be obtained by the monohalogenation of the product of formula (II) as defined above into a product of formula (P$_1$):

(P$_1$)

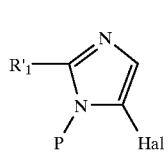

in which R'$_1$ and P have the meanings indicated above for the product of formula (II), which product of formula (P$_1$) can be reacted, after exchange according to the halogen-metal reaction known to a man skilled in the art, with a suitable electrophile, according to the methods known to a man skilled in the art and in particular as has been described above for passing from the product of formula (III) to the product of formula (V). By the same process, certain products of formulae (IX) and (XX) can also be obtained starting from the product of formula (III) as defined above. It can also be noted that the product of formula:

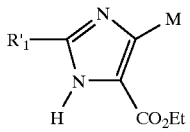

in which R'$_1$ and M have the meanings indicated above, described in EP 0,465,368, can be subjected to a thermal saponification reaction then to a decarboxylation in order to obtain a product of formula (IX) as defined above.

Such an illustration is given in the experimental part described hereafter.

The products of formula (III) in which R'$_1$ represents an alkylthio radical can be obtained either starting from the product of formula (II) as defined above as described above, or starting from commercially-available products such as in particular 2,4,5-tribromoimidazole or 4,5-dibromo 2-phenylimidazole, as has been described above for passing from the product of formula (III) to the product of formula (V).

The starting compounds of formula (VIII) may be commercially available or can be prepared according to the usual methods known to a man skilled in the art.

The starting products of formulae (IV$_a$), (IV$_b$), (IV$_c$), (IV$_d$), (IV$_e$), (XII) and (XV) are commercially available, in particular the products of formula (IV$_a$) such as sec-butyl disulphide, ethyl disulphide, isopropyl disulphide, methyl disulphide, benzyl disulphide, phenyl disulphide, propyl disulphide, the products of formula (IV$_b$) such as methyl methanethiosulphonate, the products of formula (IV$_c$) such as methyl chloroformate, benzyl chloroformate, isobutyl chloroformate, ethyl chloroformate, N-propyl chloroformate, the products of formula (IV$_d$) such as dimethyl carbonate, diethyl carbonate, the products of formula (IV$_e$) such as di-tert-butyl oxalate, diethyl oxalate, dimethyl oxalate, the products of formula (XII) such as ethyl thiophene 2-glyoxylate, ethyl 3-methyl 2-oxobutyrate, ethyl phenyl glyoxylate, methyl pyruvate, methyl benzoylformate, the products of formula (XV) such as methyl isocyanate, 2-carbomethoxyphenyl isocyanate, benzyl isocyanate, cyclohexyl isocyanate, N-propyl isocyanate, allyl isocyanate, phenyl isocyanate.

A preparation process for certain products of formula (VIII) is described in particular in the European Patent EP 0,465,368.

Examples of the preparation of compounds of formula (VIII) are also described in the literature and examples of their preparation are given in particular in the U.S. Pat. No. 4,880,804 or for example in the reference Chemistry and Industry Sep. 7, 1987 HOWARD and COLQUHOUN pp. 612–617.

The compounds of formula (I$_B$) as defined above as well as their addition salts with acids have useful pharmacological properties.

The products are endowed with antagonistic properties for the angiotensin II receptor and are thus in particular inhibitors of the effects of angiotensin II, in particular of the vasoconstrictive effect and also of the trophic effect at the level of the myocytes.

These properties justify their use in therapeutics and a subject of the invention is also, as medicaments, the products of formula (I$_B$) as defined above, said products of formula (I$_B$) being in all the possible racemic or optically active isomer forms, as well as the addition salts with pharmaceutically acceptable mineral or organic acids of said products of formula (I$_B$).

A more particular subject of invention is, as medicaments, the products described hereafter in the examples and in particular the following products of formula (I$_B$):

2-butyl alpha-hydroxy alpha-methyl 4-(methylthio)1-[(2'-(((((phenylmethoxy)carbonyl)amino)sulphonyl)(1,1'-biphenyl)4-yl)methyl]1H-imidazole 5-acetic acid, 2-butyl alpha-hydroxy alpha-methyl 4-(methylthio)1-[(2'-(((((propylamino)carbonyl)amino)sulphonyl)(1,1'-biphenyl)4-yl)methyl]1H-imidazole 5-acetic acid, 2-butyl alpha-hydroxy alpha-methyl 4-(methylthio)1-[(2'-(((((phenylmethyl)amino)carbonyl)amino)sulphonyl)(1,1'-biphenyl)4-yl)methyl]1H-imidazole 5-acetic acid, 2-butyl 1-[(2'-(((((cyclohexylmethyl)amino)carbonyl)amino)sulphonyl)(1,1'-biphenyl)4-yl)methyl]alpha-hydroxy alpha-methyl 4-(methylthio)1H-imidazole 5-acetic acid, 1-[(2'-(((((phenylmethyl)amino)sulphonyl)(1,1'-biphenyl)4-yl)methyl]alpha-hydroxy 4-(methylthio)2-propyl 1H-imidazole 5-acetic acid, sodium 1-[(2'-(((((cyclohexylmethyl)amino)carbonyl)amino)sulphonyl)(1,1'-biphenyl)4-yl)methyl]4-(methylthio)2-propyl 1H-imidazole 5-carboxylate, 4-(methylthio)1-[(2'-(((((phenylmethyl)amino)carbonyl)amino)sulphonyl)(1,1'-biphenyl)4-yl)methyl]2-propyl 1H-imidazole 5-carboxylic acid, sodium alpha-butyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate, alpha-hydroxy 4-(methylthio)alpha-phenyl 1-((2'-(((((phenylmethyl)amino)carbonyl)amino)sulphonyl)(1,1'-biphenyl)4-yl)methyl)2-propyl 1H-imidazole 5-acetic acid, 1-((2'-(((((cyclohexylmethyl)amino)carbonyl)amino)sulphonyl)(1,1'-biphenyl)4-yl)methyl)4-(difluoromethyl)thio)2-propyl 1H-imidazole 5-carboxylic acid, 4-((difluoromethyl)thio)1-((2'-(((((phenylmethyl)amino)carbonyl)amino)sulphonyl)1,1'-biphenyl)4-yl)methyl)2-propyl 1H-imidazole 5-carboxylic acid, 4-((difluoromethyl)thio)2-propyl 1-((2'-(((((2-thienylmethyl)amino)carbonyl)amino)sulphonyl)(1,1'-biphenyl)4-yl)methyl)1H-imidazole 5-carboxylic acid, as well as their pharmaceutically acceptable salts.

The medicaments, which are a subject of the invention, can be used in the treatment of cardiovascular illnesses associated with an alteration in vasomotricity or total blood volume: myocardial infarction and its consequences, cardiac insufficiency, renal insufficiency, angina pectoris, hyperaldosteronism, arterial hypertension and its consequences. These medicaments, which are a subject of the invention, could also be used for the treatment of glaucoma, atherosclerosis and different types of visceral spasms, and as neuronal protective substances or also in the prevention of post-angioplastic recurrence of stenosis.

In particular the medicaments which are a subject of the invention can be used for their anti-hypertrophic and antifibrotic effects at the cardiac and vascular levels. Quite particularly, they can be used for the treatment and the prevention of cardiovascular disorders associated with diabetes.

They can also be used in the treatment of certain gastrointestinal or gynaecological disorders and in particular for a relaxing effect on the uterus.

The medicaments which are a subject of the invention can also be used in the treatment of memory disorders and disorders of the cognitive functions, as well as anxiety.

The invention extends to the pharmaceutical compositions containing at least one of the medicaments as defined above as active ingredient.

The products of formula $(I_B)$ of the present invention therefore have an affinity not only for the $AT_1$ receptor but also for the $AT_2$ receptor of angiotensin II.

Therefore a particular subject of the invention is the use of the products of formula $(I_B)$ as defined above, for the preparation of pharmaceutical compositions intended for the treatment of illnesses resulting from an abnormal stimulation of the $AT_1$ and/or $AT_2$ receptors of angiotensin II.

The advantage which is presented by such products of formulae (I), $(I_A)$ and $(I_B)$ which possess an affinity both for the $AT_1$ receptor and for the $AT_2$ receptor is, by the simultaneous blocking of these two receptors, to increase the effectiveness, that is to say the protective effects, resulting from the administration of such products vis-à-vis the affected organs, in particular the heart, the vessels and the kidneys and also to widen the indications in particular for the non-cardiovascular organs such as the urogenital apparatus.

As the circulatory amounts of angiotensin II is increased by a phenomenon of retro-control when the $AT_1$ receptor is blocked, the simultaneous blocking of the $AT_2$ receptor would allow a better long-term effectiveness in the treatment in particular of arterial hypertension and the prevention of complications, in particular cardiac and vascular hypertrophies as well as the development of fibroses in the target organs.

The improvement of the cognitive properties of the products showing an affinity both for $AT_1$ and $AT_2$ receptors can also be underlined.

Therefore a more particular subject of the invention is the use of products of formulae (I), $(I_A)$ and $(I_B)$ as defined above, for the preparation of pharmaceutical compositions intended for the treatment of arterial hypertension, cardiac insufficiency and post-angioplastic recurrence of stenosis.

A quite particular subject of the invention is the use of the products of formulae (I), $(I_A)$ and $(I_B)$ as defined above, for the preparation of pharmaceutical compositions intended for the treatment of renal insufficiency.

A subject of the invention is also the use of the products of formulae (I), $(I_A)$ and $(I_B)$ as defined above, for the preparation of pharmaceutical compositions intended for the treatment and for the prevention of cardiovascular disorders associated with diabetes.

The pharmaceutical compositions indicated above can be administered by buccal, rectal route, by parenteral route or by local route as a topical application on the skin and mucous membranes or by injection by intravenous or intramuscular route.

These compositions can be solid or liquid and can be presented in all the pharmaceutical forms commonly used in human medicine such as, for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according to the product used, the subject being treated and the illness in question, can be, for example, from 1 to 100 mg per day for an adult, by oral route.

The following examples illustrate the invention without however limiting it.

Preparation 1
ethyl 2-butyl alpha-hydroxy alpha-methyl 1-[(2'-((((dimethylamino)methylene)amino)sulphonyl)(1,1'-biphenyl)4-yl)methyl]4-(methylthio)1H-imidazole 5-acetate Stage A
4'-[(2-butyl 4-(methylthio)1H-imidazol 1-yl)methyl]N-[(dimethylamino)methylene](1,1'-biphenyl)2-sulphonamide a)2-butyl 4-(methylthio)1H-imidazole 760 mg of ethyl 2-n-butyl 4-methylthio imidazole 5-carboxylate, prepared as described in the European Patent Application EP 0,465,368, is introduced into 15 cm³ of NaOH (2N). The mixture is taken to reflux and agitated for 24 hours. After cooling down, dilution is carried out with 50 cm³ of $H_2O$, followed by extraction with 3×20 cm³ $CH_2Cl_2$, washing with 20 cm³ $H_2O$ and drying. 535 mg of expected product is obtained.

M.p.=64° C.

IR Spectrum (CHCl₃)

Absence of C=O

=C—NH 3452 cm⁻¹

Conjugated system 1596–1502 cm⁻¹ b)4'-[(2-butyl 4-(methylthio)1H-imidazol 1-yl)methyl]N-[(dimethylamino)methylene](1,1'-biphenyl)2-sulphonamide 5 g of 2-butyl 4-(methylthio)1H-imidazole is dissolved in 120 cm³ of THF. 1.55 g of 50% sodium hydride dispersed in oil is then added slowly to the orange-coloured solution obtained. The temperature is increased to 25° C. The reaction medium is agitated for 30 minutes at this temperature then 14 g of 4'-bromomethyl N-[(dimethylamino)methylene](1,1'-biphenyl)2-sulphonamide is introduced. Agitation is carried out at ambient temperature until evolution is complete, that is for about 3 hours. The resultant product is taken up in water, extraction is carried out with ethyl acetate, followed by separation by chromatography on silica, eluting with ethyl acetate then impasting in iso ether, filtration and drying. In this way 9.35 g of the expected product (colourless crystals) is obtained. M.p.=148° C.

| IR Spectrum: CHCl₃ | |
|---|---|
| Absence of =C—NH— | |
| —SO₂—N=C—N< | 1627 cm⁻¹ |
| armoatic, heteroaromatic | 1593–1564–1516–1500 cm⁻¹ |

Stage B
4'-[(5-bromo 2-butyl 4-(methylthio)1H-imidazol 1-yl)methyl]N-[(dimethylamino)methylene](1,1'-biphenyl)2-sulphonamide 10.4 g of the product obtained in Stage A above is dissolved in 450 cm³ of CH₂Cl₂ and 3.9 g of N-succinimide is added.

The mixture is agitated for about 15 minutes at ambient temperature, washed with water and with salt water, followed by decanting, drying, filtration and driving off the solvent under vacuum at 50° C.

The residue is impasted in iso ether, filtered and dried. 11.8 g of expected product (colourless crystals) is obtained, M.p.=158° C.

| IR Spectrum: CHCl₃ | |
|---|---|
| 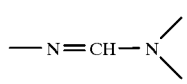 | 1628 cm⁻¹ |
| armoatic and heteroaromatic | 1592–1568 cm⁻¹ |
| Microanalysis: | |
| % calculated | Br 14.54 |
| % found | 14.4–14.7 |

Stage C
ethyl 2-butyl alpha-hydroxy alpha-methyl 1-[(2'-((((dimethylamino)methylene)amino)sulphonyl)(1,1'-biphenyl)4-yl)methyl]4-(methylthio)1H-imidazole 5-acetate 11.8 g of the product obtained in Stage B above is dissolved in 160 cm³ of THF. Then 17.5 cm³ of a 1M solution of isopropyl magnesium chloride in solution in ether is added without exceeding 25° C. After agitation for about 30 minutes at ambient temperature, 4 cm³ of ethyl pyruvate is added slowly. Agitation is carried out for about one hour at ambient temperature, 1 cm³ of ethyl pyruvate is added and agitation is continued for about one more hour.

The resultant product is taken up in 200 cm³ of NH₄Cl in 10% solution and extraction is carried out with ethyl acetate. The extracts are dried, concentrated to about 200 cm³, and the crystals obtained are filtered off and dried.

6 g of expected product (colourless crystals) is obtained. M.p.=208–210° C.

| IR Spectrum: CHCl₃ | |
|---|---|
| Complex OH | ~3530 cm⁻¹ |
| C=O | 1722 cm⁻¹ |
| C=N | 1626 cm⁻¹ |
| Heterocycle + aromatic | 1565, 1518 cm⁻¹ |
| UV Spectrum: | |
| 1) In EtOH | |
| infl. 274 nm | ε = 3100 |
| infl. 231 nm | ε = 23000 |
| 2) In EtOH - HCl N/10 | |
| infl. 228 nm | ε = 30000 |
| infl. 273 nm | ε = 3400 |

Preparation 2
ethyl 2-methyl 4-(methylthio)1-[(2'-((((dimethylamino)methylene)amino)sulphonyl)(1,1'-biphenyl)4-yl)methyl] alpha-oxo 1H-imidazole 5-acetate
Stage A
4,5-dibromo 2-methyl 1-[(2-(trimethylsilyl)ethoxy)methyl] 1H-imidazole The product is obtained by 2 consecutive reactions.

1) Protection stage of the 2-methyl imidazole
6.8 g of 2-methyl imidazole is dissolved in 250 cm³ of THF and 4 g of sodium hydride at 50% in oil is added in small fractions. As the reaction is exothermic, the temperature of the medium is maintained at ambient temperature for about 30 minutes.

17.5 cm³ of SEM chloride is then added dropwise into the reaction medium. After about 20 minutes of agitation at 20° C., the excess sodium hydride is hydrolyzed by the addition of THF with 20% H₂O.

The solution obtained is brought to dryness, followed by taking up in ethyl acetate and washing with water. The organic phase thus collected is dried. A yellow oil is obtained which is purified by chromatography on silica with CH₂Cl₂-methanol (90-10) as eluant.

In this way 14 g of protected product is obtained.
2) Bromination
The protected product obtained above is dissolved in 250 cm³ of CH₂Cl₂. Next 25 g of N-bromo succinimide is added to this solution in small fractions.

Agitation is maintained for about 30 minutes at ambient temperature. The organic phase is washed with a sodium bicarbonate solution, then abundantly with water. After drying and evaporation, 13.4 g of expected product (homogeneous yellow oil) is recovered.

| IR Spectrum: CHCl₃ | |
|---|---|
| Absence of =C—NH— Conjugated system | 1520 cm⁻¹ |
| 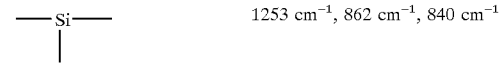 | 1253 cm⁻¹, 862 cm⁻¹, 840 cm⁻¹ |

Stage B
ethyl 2-methyl 1-[(2-(trimethylsilyl)ethoxy)methyl]5-(methylthio)alpha-oxo 1H-imidazole 4-acetate 3 g of the product obtained in Stage A above is dissolved under an anhydrous atmosphere in 20 cm³ of anhydrous THF. This solution is then cooled down to −78° C. and while maintaining the temperature at −78° C., 5.6 cm³ of 1.5 molar n-butyl lithium in hexane is added to it. Agitation is maintained at −78° C. for about 10 minutes.

Next 0.76 cm³ of dimethyl disulphide is introduced, then the temperature is left to rise slowly to 20° C. and agitation is carried out for about 30 minutes.

The reaction medium is cooled down again to −78° C., and 5.6 cm³ of 1.5 M n-butyl lithium in hexane is added to it as previously. After agitation for about 10 minutes at −78° C., 5.5 cm³ of diethyl oxalate is introduced in one go. Agitation is maintained at ambient temperature for about 30 minutes. The reaction medium is then poured into ice-cooled water. Extraction is carried out with ethyl acetate, the organic phase is washed with a sodium bicarbonate solution then with water and dried. A brown oil is recovered, which is purified by chromatography on silica with ethyl acetate-cyclohexane (50-50) as eluant. 1.63 g of expected product (oil) is obtained.

| IR Spectrum: CHCl₃ | |
|---|---|
| C=O | 1738–1673 cm⁻¹ |
| Conjugated system | 1538 cm⁻¹ |

IR Spectrum: CHCl₃

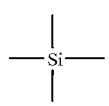  1502 cm⁻¹

Stage C
ethyl 2-methyl 5-(methylthio)alpha-oxo 1H-imidazole 4-acetate 1.6 g of the product obtained in Stage B above is dissolved in 30 cm³ of CH₂Cl₂, and 10 cm³ of trifluoroacetic acid is added. The reaction medium is then taken to reflux for about 10 hours. The solution is then brought to dryness, and the residue is taken up in water. The aqueous phase is alkalinized by the addition of sodium bicarbonate, followed by extraction with ethyl acetate, washing with water then drying and 920 mg of expected product (yellow oil) is recovered, used as it is in the next stage of the synthesis.

IR Spectrum: CHCl₃

| | |
|---|---|
| —C—NH | 3415 cm⁻¹ |
| C=O | 1716–1633 cm⁻¹ |
| Conjugated system | 1530–1502 cm⁻¹ |

Stage D
ethyl 2-methyl 4-(methylthio)1-[(2'-((((dimethylamino)methylene)amino)sulphonyl)( 1,1'-biphenyl)4-yl)methyl] alpha-oxo 1H-imidazole 5-acetate 880 mg of the product obtained in Stage C above is dissolved in 10 cm³ of anhydrous DMF and 800 mg of potassium carbonate then 2.2 g of 4'-bromomethyl N-[(dimethylamino)methylene](1,1'-biphenyl)2-sulphonamide are added successively. Agitation is maintained for about 3 hours at ambient temperature. The yellow suspension thus obtained is poured into water. Extraction is carried out with ethyl acetate, the extracts are washed with water then dried and a yellow resin is recovered which is purified on silica with ethyl acetate as eluant.

In this way 1.17 g of expected product is obtained.

IR Spectrum: CHCl₃

| | |
|---|---|
| Absence of =C—NH | |
| Ester C=O | 1735 cm⁻¹ |
| Other C=O | 1629 cm⁻¹ (F) |
| C=N | |
| Aromatic | 1570 cm⁻¹ |
| Heteroatom | 1516 cm⁻¹ |

Preparation 3
ethyl 1-[(2'-(aminosulphonyl)(1,1'-biphenyl)4-yl)methyl]4-(methylthio)alpha-oxo 2-propyl 1H-imidazole 5-acetate

Stage A
4,5-dibromo 2-n-propyl 1-[(2-(trimethylsilyl)ethoxy)methyl]1H-imidazole The process is carried out as in Stage A of Preparation 2, replacing 2-methyl 1H-imidazole with 2-propyl 1H-imidazole.

The product is obtained by 2 consecutive reactions.

1) Protection stage of 2-propyl imidazole 30 g of 2-propyl imidazole is dissolved in 500 cm³ of THF and 12.5 g of sodium hydride at 50% in oil is added in small fractions.

53 cm³ of SEM chloride is then added to the reaction medium, and hydrolysis is carried out using THF with 20% H₂O.

In this way 57.3 g of protected product is obtained.

2) Bromination

The protected product obtained above is dissolved in 500 cm³ of CH₂Cl₂. 93.5 g of N-bromo succinimide is added and 93.7 g of expected product is obtained.

IR Spectrum: CHCl₃

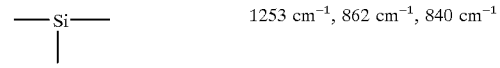

| | |
|---|---|
| Absence of =C—NH— Conjugated system | 1520 cm⁻¹ |
| —Si— | 1253 cm⁻¹, 862 cm⁻¹, 840 cm⁻¹ |

Stage B
ethyl 2-n-propyl 1-[(2-(trimethylsilyl)ethoxy)methyl]5-(methylthio)alpha-oxo 1H-imidazole 4-acetate 36.7 g of the product obtained in Stage A above is introduced under an anhydrous atmosphere into 200 cm³ of THF, 63.7 cm³ of 1.5 M n-butyl lithium in hexane then 8.62 cm³ of dimethyl disulphide are added at –78° C., the whole is left to rise to ambient temperature. Then 63.7 cm³ of 1.5 molar n-butyl lithium in hexane followed by 55 cm³ of ethyl oxalate are added as previously at –78° C. 11.75 g of expected product is obtained.

IR Spectrum: CHCl₃

| | |
|---|---|
| C=O | 1737–1672 cm⁻¹ |
| Conjugated system | 1527 cm⁻¹ |
| | 1501 cm⁻¹ |

Stage C
ethyl 2-n-propyl 5-(methylthio)alpha-oxo 1H-imidazole 4-acetate

The process is carried out as in Stage C of Preparation 2 starting with 11 g of the product obtained in Stage B above in 200 cm³ of CH₂Cl₂, and 40 cm³ of trifluoroacetic acid. 7.15 g of expected product is obtained.

IR Spectrum: CHCl₃

| | |
|---|---|
| =C—NH | 3413 cm⁻¹ |
| C=O | 1714–1633 cm⁻¹ |
| Conjugated system | 1524–1492 cm⁻¹ |

Stage D
ethyl 2-n-propyl 4-(methylthio)1-[(2'-((((dimethyl-amino)methylene)amino)sulphonyl)(1,1'-biphenyl)4-yl)methyl] alpha-oxo 1H-imidazole 5-acetate The process is carried out as in Stage D of Preparation 2 starting with 7 g of the product obtained in Stage C above in 100 cm³ of DMF and 7.5 g of potassium carbonate and 15.6 g of 4'-(bromomethyl)N-[(dimethylamino)methylene](1,1'-biphenyl)2-sulphonamide. In this way 7.83 g of expected product is obtained.

| IR Spectrum: CHCl₃ | |
|---|---|
| Absence of =C—NH | |
| Ester C=O | 1735 cm⁻¹ |
| Other C=O | 1630 cm⁻¹ (F) |
| C=N | |

Stage E
ethyl 1-[(2'-(aminosulphonyl)(1,1'-biphenyl)4-yl)methyl]2-propyl 4-(methylthio)alpha-oxo 1H-imidazole 5-acetate The process is carried out as in Stage A of Example 2 starting with 7.8 g of the product obtained in Stage D above, in 100 cm³ of ethanol and 30 cm³ of concentrated HCl and in this way 3.6 g of expected product is obtained.

| IR Spectrum CHCl₃ | |
|---|---|
| —NH₂ | 3443–3343 cm⁻¹ |
| C=O | 1734–1627 cm⁻¹ |
| Aromatic | 1593 cm⁻¹ |
| Heteroatom | 1565 cm⁻¹ |
| NH₂ def. | 1542 cm⁻¹ |

Preparation 4
S-methyl 1-[(2'-(aminosulphonyl)(1,1'-biphenyl)4-yl)methyl]2-butyl 4-(methylthio)alpha-oxo 1H-imidazole 5-ethane thioate Stage A
4'-[(2-butyl 5-((methylsulphinyl)acetyl)4-(methylthio)1H-imidazol 1-yl)methyl](1,1'-biphenyl)2-sulphonamide First of all the anion of DMSO is prepared by introducing 3.36 g of sodium hydride at 50% in oil. The NaH is removed from its oil by 3 successive washings with pentane. Then drying is carried out and 70 cm³ of anhydrous dimethylsulphoxide is added and the mixture is taken to 75° C., for about one hour. The temperature is then lowered to 0° C. and 70 cm³ of anhydrous THF and 9.5 g of ethyl 2-butyl 1-[(2'-((((dimethylamino)methylene)amino)sulphonyl)(1,1'-biphenyl)4-yl)methyl]4-(methylthio)1H-imidazole 5-carboxylate, prepared as indicated in the European Patent Application EP 0,503,162, dissolved in 70 cm³ of anhydrous THF, are added to the anion of the DMSO thus formed. The reaction medium is then left to return to ambient temperature and agitated for about half an hour. The reaction mixture is then poured into 400 cm³ of H₂O.

The solution is acidified until a pH 2 is obtained with 2N HCl. Extraction is carried out with 4×200 cm³ of methylene chloride and the organic phase is washed with 4×100 cm³ of distilled H₂O. The organic phase is dried, followed by filtration and evaporation.

Purification is carried out on silica with CH₂Cl₂-methanol (9-1) as eluant and 7.5 g of expected product is recovered.

| IR Spectrum in CHCl₃ | |
|---|---|
| Absence of SO₂N=N⟨ | |
| NH₂ | 3440–3340 cm⁻¹ |
| C=O | 1628 cm⁻¹ |
| Aromatic + Heterocycle | 1545–1525–1495 cm⁻¹ |

| IR Spectrum in CHCl₃ | |
|---|---|
| SO₂ | 1345–1165 cm⁻¹ |
| SO | 1050 cm⁻¹ |

Stage B
4'-[[5-[bromo(methylsulphinyl)acetyl]2-butyl 4-(methylthio)1H-imidazol 1-yl]methyl](1,1'-biphenyl)2-sulphonamide 1 g of the product obtained in Stage A above and 530 mg of K₂CO₃ are mixed together. Then 10 cm³ of anhydrous CH₂Cl₂ is added, the temperature of the medium is taken to 0° C. and 342 mg of N-bromo succinimide, dissolved in the minimum of anhydrous CH₂Cl₂, is added dropwise. 100 cm³ of CH₂Cl₂ is then added and the organic phase is washed with 3×200 cm³ of distilled water, and 1×100 cm³ of saturated NaCl. Drying is carried out followed by filtration and concentration to dryness.

1.09 g of expected product is obtained.

| IR Spectrum in CHCl₃ | |
|---|---|
| NH₂ | 3440–3344 cm⁻¹ |
| >=O | 1634 cm⁻¹ |
| Conj. system + Aromatic + NH₂ | 1542–1520 cm⁻¹ |

Stage C
S-methyl 1-[(2'-(aminosulphonyl)(1,1'-biphenyl)4-yl)methyl]2-butyl 4-(methylthio)alpha-oxo 2-propyl 1H-imidazole 5-ethane thioate 6.8 g of the product obtained in Stage B above is dissolved in 60 cm³ of a 25 cm³ TFA-75 cm³ CH₂Cl₂ mixture and taken to the reflux of the methylene chloride, for about 5 hours. The reaction is treated by neutralizing with a saturated solution of NaHCO₃ to a pH of 5–6, extraction is carried out with 2×200 cm³ of ethyl acetate, the extracts are washed with 1×100 cm³ of saturated NaCl, dried, filtered and concentrated to dryness. Purification is carried out on silica, with AcOEt-cyclohexane (5-5) as eluant. In this way 2.7 g of expected product is recovered.

| IR Spectrum in CHCl₃ | |
|---|---|
| NH₂ | 3445–3350 cm⁻¹ |
| >=O | 1670–1614 cm⁻¹ |
| Aromatic + heteroaromatic + NH₂ dif. | 1542 cm⁻¹–1518 cm⁻¹ |

Preparation 5
ethyl 1-[(2'-(aminosulphonyl)(1,1'-biphenyl)4-yl)methyl]4-(methylthio)2-propyl 1H-imidazole 5-carboxylate Stage A
ethyl cyano-[(1-oxobutyl)amino]acetate 5 g of ethyl(hydroxyimino)cyanoacetate, 40 cm³ of tetrahydrofuran, 11.5 cm³ of butyric anhydride and 2.5 g of platinum are mixed together and agitated under a hydrogen atmosphere until saturation. Filtration is carried out, followed by rinsing with 5×15 cm³ of ethyl ether, the ether is evaporated off, 200 cm³ of essence G is added little by little, followed by separation, washing with 3×10 cm³ of essence G and drying at about 75° C. After concentration to about 10 cm³, 50 cm³ of essence G is added, crystallization is allowed to take place for 30 minutes at ambient temperature, the crystals are separated off, washed with 3×3 cm³ of essence G and dried at about 75° C. 5.73 g of product is obtained. M.p.=110° C. Recrystallization for analyses:

540 mg of the product obtained is dissolved in 50 cm³ of isopropyl ether under reflux, the solution is filtered, concentrated, left at rest at ambient temperature for about one hour, followed by separation, washing with isopropyl ether and drying. 440 mg of expected product is obtained.
M.p.=110° C.
Microanalysis for $C_9H_{14}N_2O_3$=198.22

|  | C | H | N | O |
|---|---|---|---|---|
| % calculated | 54.53 | 7.12 | 14.13 | 24.22 |
| % found | 54.5 | 7.2 | 14.0 |  |
| IR Spectrum CHCl₃ | | | | |
| =C—NH | ~3430 cm⁻¹ | | | |
| —C≡NH | ~2245 cm⁻¹ | | | |
| —C=O | 1758 cm⁻¹ ester | | | |
|  | 1692 cm⁻¹ amide | | | |
| Amide II | 1492 cm⁻¹ | | | |

Stage B
ethyl 3-amino 2-[(1-oxobutyl)amino]3-(methylthio)2-propenoate 1.4 ml of triethylamine is added to a solution of 20 g of the nitrile obtained in Stage A above, in 400 ml of ethanol, the resultant mixture is cooled down to about −10° C. and about 22 g of methylmercaptan is bubbled through. Agitation is carried out for about 72 hours at 0° C. The excess methanethiol is eliminated, the ethanol is driven off, the residue is impasted in essence G, filtered and dried. 24.3 g of expected product (colourless crystals) is obtained.
M.p.$_{K115}$=120–124° C.
Microanalysis for $C_{10}H_{18}N_2O_3S$=246.33

|  | C | H | N | S | O |
|---|---|---|---|---|---|
| % calculated | 48.76 | 7.37 | 11.37 | 13.02 | 19.49 |
| % found | 48.6 | 7.5 | 11.4 | 12.6 | — |
| IR Spectrum CHCl₃ | | | | | |
| =C—NH₂ | 3500, 3412 cm⁻¹ | | | | |
| =C—NH | 3365, 3275 cm⁻¹ | | | | |
| Complex C=O | 1665 cm⁻¹ | | | | |
| C—C and NH₂ def. | 1592 cm⁻¹ | | | | |
| Amide II | 1488 cm⁻¹ | | | | |
| UV Spectrum in EtOH | | | | | |
| Max. 220 nm | ε = 5500 | | | | |
| Max. 291–292 | ε = 19400 | | | | |

Stage C
ethyl 4-(methylthio)2-propyl 1H-imidazole 5-carboxylate

A solution of 12.9 g of 4-dimethylaminopyridine in 90 cm³ of methylene chloride is added to 20.1 g of phosphorus pentachloride in 300 cm³ of methylene chloride, cooled down to about −70° C.

The resultant mixture is maintained for about another 15 minutes at about −70° C. then a solution of 12 g of the product obtained in Stage B above in 120 cm³ of methylene chloride is introduced. The whole is left to return to ambient temperature and maintained under agitation for about 22 hours.

The reaction mixture is poured into 2.5 l of water+ice and neutralized by the addition of about 60 g of sodium bicarbonate. Agitation is continued for about 30 minutes, followed by decanting and extraction with 500 cm³ of CH₂Cl₂. The extracts are washed with salt water, dried and the solvent is driven off at about 50° C. Purification is carried out by chromatography on silica with CH₂Cl₂-AcOEt (90-10) then CH₂Cl₂-AcOEt (80-20) as eluants. The solvents are driven off at about 50° C., the residue is impasted in essence G, filtered and dried. 7.4 g of expected product (colourless crystals) is obtained.
M.p.$_{K95}$=85° C.
Microanalysis
Concordance for $C_{10}H_{16}N_2O_2S$=228.32

|  | H | N | S | O |
|---|---|---|---|---|
| % calculated | 52.61 | 7.06 | 12.27 | 14.04 | 14.02 |
| % found | 52.7 | 7.3 | 12.2 | 14.0 | |
| IR Spectrum CHCl₃ | | | | |
| —C—NH | 3440–3260 cm⁻¹ | | | |
| Complex C=O max. ~1672 cm⁻¹ | | | | |
| Heterocycle | 1542–1498 cm⁻¹ | | | |
| UV Spectrum in EtOH | | | | |
| Max. 213–214 nm | ε = 14500 | | | |
| Infl. 229 nm | ε = 7200 | | | |
| Max. 286 nm | ε = 12200 | | | |
| UV Spectrum in EtOH/HCl N/10 | | | | |
| Max. 238 nm | ε = 6800 | | | |
| Max. 277 nm | ε = 9600 | | | |
| by basic return --> max. 296 nm. | | | | |

Stage D
ethyl 1-[(2'-((((dimethylamino)methylene)amino) sulphonyl)(1,1'-biphenyl)4-yl)methyl]4-(methylthio)2-propyl 1H-imidazole 5-carboxylate 8.1 g of the product obtained in Stage C above is dissolved in 80 cm³ of dimethylformamide and 16.1 g of 4'-(bromomethyl)N-[(dimethylamino)methylene](1,1'-biphenyl)2-sulphonamide and 4.9 g of potassium carbonate are added. The mixture is agitated at ambient temperature for about 24 hours. The DMF is driven off at 50° C., the remaining product is impasted in water, followed by filtration, washing with water and drying at about 60° C.

The residue is impasted in 240 cm³ of AcOEt, under agitation for about 30 minutes at about 50° C., 160 cm³ of hexane is added, followed by filtration and drying. 14 g of expected product (colourless crystals) is obtained.
M.p.$_{K163}$: 182° C.

| IR Spectrum CHCl₃ Absence of =C—NH | |
|---|---|
| C=O | 1690 cm⁻¹ |
| C=N | 1628 cm⁻¹ |
| Heterocycle | 1504–1565 cm⁻¹ |
| UV Spectrum in EtOH | |
| Infl. 230 nm | ε = 32000 |
| Max. 287 nm | ε = 15500 |

Stage E
ethyl 1-[(2'-(aminosulphonyl)(1,1'-biphenyl)4-yl)methyl]4-(methylthio)2-propyl 1H-imidazole 5-carboxylate 11.2 g of the product obtained in Stage D above is mixed with 200 cm³ of ethanol and 100 cm³ of concentrated hydrochloric acid. The mixture is heated under reflux for about 2 hours. The ethanol is evaporated off, dilution is carried out by the addition of 400 cm³ of water, followed by alkalinization under agitation by the addition of caustic soda lye and extraction with ethyl acetate. The extracts are washed with water and with salt water, followed by drying, filtration and driving off the solvent at about 50° C.

The residue is purified by chromatography on silica with AcOEt 60 Hexane 40 as eluant. 9.3 g of expected product (colourless crystals) is obtained. M.p.$_{K135}$=130–132° C.

| IR Spectrum: CHCl$_3$ Absence of starting product | |
|---|---|
| C=O | 1689 cm$^{-1}$ |
| NH$_2$ | 3444–3340 cm$^{-1}$ |
| Conjugated system | |
| + aromatic | 1618–1590–1560–1540–1508 cm$^{-1}$ |
| NH$_2$ def. | |
| UV Spectrum in EtOH | |
| Infl. 210 nm | ε = 45000 |
| Infl. 234 nm | ε = 17000 |
| Max. 286 nm | ε = 15000 |

EXAMPLE 1
ethyl 1-[(2'-(aminosulphonyl)(1,1'-biphenyl)4-yl)methyl]2-butyl alpha-hydroxy alpha-methyl 4-(methylthio)1H-imidazole 5-acetate 1.24 g of the product obtained in Preparation 1, 30 cm$^3$ of 95% ethanol and 10 cm$^3$ of concentrated HCl are mixed together.

The solution obtained is heated under reflux until total conversion is achieved, that being for about 2 hours.

The reaction medium is cooled down, diluted with water, alkalinized by the addition of cNaOH, the aqueous phase is saturated with K$_2$CO$_3$, extraction is carried out with AcOEt, followed by purification by chromatography on silica with AcOEt as solvent. 930 mg of expected product (straw coloured resin) is obtained.

| IR Spectrum CHCl$_3$ | |
|---|---|
| Absence of 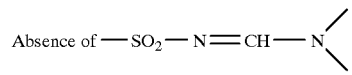 | |
| OH | ~3520 cm$^{-1}$ complex |
| NH$_2$ | ~3442 cm$^{-1}$, ~3355 cm$^{-1}$ |
| C=O | 1721 cm$^{-1}$ |
| Aromatic | 1614 cm$^{-1}$ |
| Heteroaromatic | 1592 cm$^{-1}$ |
| NH$_2$ | 1565–1543–1517 cm$^{-1}$ |

EXAMPLE 2
ethyl 2-butyl 1-[(2'-(((ethoxycarbonyl)amino)sulphonyl)(1,1'-biphenyl)4-yl)methyl]alpha-methylene 4-(methylthio)1H-imidazole 5-acetate
Stage A
ethyl 1-[(2'-(aminosulphonyl)(1,1'-biphenyl)4-yl)methyl]2-butyl alpha-methylene 4-(methylthio)1H-imidazole 5-acetate 5.7 g of the product obtained in Preparation 1 is introduced into 300 cm$^3$ of dioxane and 30 cm$^3$ of concentrated sulphuric acid is added. The solution is heated under reflux for about 5 hours. It is taken up in water and AcOEt, followed by alkalinization with concentrated soda, saturation by the addition of K$_2$CO$_3$ and extraction is carried out with AcOEt. Purification is carried out on silica with AcOEt-CH$_2$Cl$_2$ (60-40) as eluant and 1.33 g of expected product is obtained.

Stage B
ethyl 2-butyl 1-[(2'-(((ethoxycarbonyl)amino)sulphonyl)(1,1'-biphenyl)4-yl)methyl]alpha-methylene 4-(methylthio)1H-imidazole 5-acetate 1 g of the product obtained in Stage A above is mixed with 15 cm$^3$ of dimethoxyethane, 550 mg of K$_2$CO$_3$ and 0.4 cm$^3$ of ethyl chloroformate. The mixture is heated under reflux for about one hour, diluted with water and extraction is carried out with AcOEt. The extracts are purified on silica with AcOEt-hexane (60-40) as eluant, then eluted with CHCl$_3$ with 2% MeOH and 720 mg of expected product is recovered.

EXAMPLE 3
2-butyl alpha-methylene 4-(methylthio)1-((2'-(((ethoxycarbonyl)amino)sulphonyl)(1,1'-biphenyl)4-yl)methyl)1H-imidazole 5-acetic acid 650 mg of the product of Example 2 in 10 cm$^3$ of dioxane with 5 cm$^3$ of 2N NaOH is agitated at ambient temperature for 6 hours. The mixture is diluted with water, a neutral fraction is extracted with AcOEt, followed by acidification by the addition of cHCl and extraction with AcOEt. First of all the extracts are purified on silica with CHCl$_3$-MeOH (80-20) as eluant, the solvents are driven off, followed by impasting in iso ether, filtration and drying at ambient temperature. 200 mg of the acid obtained is dissolved in 10 cm$^3$ of 2N NaOH and the solution is diluted with 10 cm$^3$ of water.

After filtration, the aqueous phase is washed with ether, then acidified by the addition of cHCl. Extraction is carried out with AcOEt, the extracts are washed with salt water, dried, filtered and the solvent is driven off. The remaining product is impasted in essence G, filtered and dried at ambient temperature. 118 mg of expected product is obtained.

Microanalysis concordance for C$_{27}$H$_{31}$N$_3$O$_6$S$_2$=557.69

| | C | H | N | S |
|---|---|---|---|---|
| % calculated | 58.15 | 5.60 | 7.53 | 11.50 |
| % found | 57.8 | 5.7 | 7.7 | 11.9 |

EXAMPLE 4
1-[(2'-(aminosulphonyl)(1,1'-biphenyl)4-yl)methyl]2-butyl 4-(methylthio)alpha-methylene 1H-imidazole 5-acetic acid
Stage A
1-[(2'-(aminosulphonyl)(1,1'-biphenyl)4-yl)methyl]2-butyl alpha-hydroxy alpha-methyl 4-(methylthio)1H-imidazole 5-acetic acid 5.9 g of the product obtained in Preparation 1 is introduced into 300 cm$^3$ of dioxane and 30 cm$^3$ of 50% dilute sulphuric acid is added. The solution is heated to about 100° C. and agitated for about 3 hours. The dioxane is evaporated off, dilution is carried out with water followed by extraction with CHCl$_3$ with 20% of MeOH. After purification on silica with CHCl$_3$-MeOH (80-20) as eluant, 4.5 g of expected product is recovered.
Stage B
1-[(2'-(aminosulphonyl)(1,1'-biphenyl)4-yl)methyl]2-butyl 4-(methylthio)alpha-methylene 1H-imidazole 5-acetic acid 1 g of the product obtained in Stage A above is introduced into 50 cm$^3$ of dioxane and 5 cm$^3$ of concentrated sulphuric acid is added. The solution is heated for about 5 hours, diluted with water, saturated with NaCl and extraction is carried out with CHCl$_3$ with 20% MeOH.

Purification is carried out on silica with CHCl$_3$-MeOH (80-20) as eluant and 595 mg of expected product is obtained.

EXAMPLE 5

2-butyl alpha-methylene 4-(methylthio)1-((2'-((((propylamino)carbonyl)amino)sulphonyl)(1,1'-biphenyl)4-yl)methyl)1H-imidazole 5-acetic acid (sodium salt)

0.12 cm³ of propyl isocyanate is added to a mixture of 545 mg of the product of Example 4 and 310 mg of $K_2CO_3$ in 20 cm³ of acetone heated under reflux, then reflux is continued for about 3 hours.

Part of the acetone is driven off, followed by dilution with water, saturation by the addition of NaCl after acidification by cHCl and extraction with $CHCl_3$ with 20% MeOH. Purification is carried out on silica with $CHCl_3$-MeOH (80-20) as eluant, followed by dissolution in 20 cm³ of 2N NaOH and acidification under agitation by the addition of cHCl to a pH of 1. Agitation is carried out at ambient temperature for about 3 hours, followed by filtration, washing with water until neutrality and drying. 190 mg of expected product is obtained.

Microanalysis concordance for $C_{23}H_{33}N_4NaO_5S_2$=592.72

|  | C | H | N | S |
|---|---|---|---|---|
| % calculated | 56.74 | 5.61 | 9.45 | 10.82 |
| % found | 56.6 | 5.7 | 9.7 | 11.1 |

EXAMPLE 6 ethyl 2-butyl alpha-hydroxy alpha-methyl 4-(methylthio)1-[(2'-((((phenylmethoxy)carbonyl)amino)sulphonyl)(1,1'-biphenyl)4-yl)methyl]1H-imidazole 5-acetate 138 mg of $K_2CO_3$ and 0.08 cm³ of benzyl chloroformate are added to a solution of 265 mg of the product of Example 1 in 4 cm³ of dimethoxyethane. The resultant mixture is heated under reflux for 30 minutes, diluted with water, extraction is carried out with AcOEt and the extracts are purified on silica with $CHCl_3$-MeOH (95-5) as eluant. 180 mg of expected product is recovered.

EXAMPLE 7

2-butyl alpha-hydroxy alpha-methyl 4-(methylthio)1-[(2'-((((phenylmethoxy)carbonyl)amino)sulphonyl)(1,1'-biphenyl) 4-yl)methyl]1H-imidazole 5-acetic acid 311 mg of the product of Example 6 is introduced into 10 cm³ of MeOH, 10 cm³ of 2N NaOH is added and the whole is agitated for about 2 hours at ambient temperature. The aqueous phase is extracted with ether then acidified to pH 1 by the addition of cHCl followed by extraction with $CHCl_3$ with 20% MeOH, then evaporation. The resultant product is redissolved in 10 cm³ of 2N soda and 15 cm³ of water, followed by filtration, acidification by the addition of cHCl, filtration, washing with water and with essence G and drying. 216 mg of expected product is obtained. M.p.= 140–150° C.

IR Spectrum: Nujol

Complex absorption OH/NH region

| C=O | 1744 cm⁻¹ complex |
|---|---|
| Aromatic | 1620 cm⁻¹ |
| Heteroaromatic | 1591 cm⁻¹ |
| Amide | 1500 cm⁻¹ |

Microanalysis concordance for $C_{32}H_{35}N_3O_7S_2$=637.78

|  | C | H | N | S | O |
|---|---|---|---|---|---|
| % calculated | 60.26 | 5.53 | 6.59 | 10.05 | 17.56 |
| % found | 59.95 | 5.3 | 6.6 | 10.4 |  |

EXAMPLE 8 ethyl 2-butyl alpha-hydroxy alpha-methyl 4-(methylthio)1-[(2'-((((propylamino)carbonyl)amino)sulphonyl)(1,1'-biphenyl)4-yl)methyl]1H-imidazole 5-acetate 1.3 g of the product of Example 1 is introduced into 40 cm³ of acetone and 680 mg of potassium carbonate is added. The resultant mixture is heated under reflux, 0.25 cm³ of propyl isocyanate is added and reflux is continued for about 2 hours, followed by cooling, filtration, washing with acetone and driving off the solvent. Purification is carried out on silica with $CHCl_3$-MeOH (98-2) as eluant. The residue is impasted in iso ether, followed by filtration and drying at ambient temperature. 170 mg of expected product is obtained.

| IR Spectrum: $CHCl_3$ | |
|---|---|
| OH | 3510 cm⁻¹ complex |
| =C—NH | 3403 cm⁻¹ + associated |
| >=O | 1707 cm⁻¹ |
| Amide II | 1615 cm⁻¹ |
| Aromatic | 1603 cm⁻¹ |
| Heteroaromatic | 1539 cm⁻¹ (F). |

EXAMPLE 9

2-butyl alpha-hydroxy alpha-methyl 4-(methylthio)1-[(2'-((((propylamino)carbonyl)amino)sulphonyl)(1,1'-biphenyl) 4-yl)methyl]1H-imidazole 5-acetic acid 5 cm³ of 2N NaOH is added to a solution of 582 mg of the product of Example 8 in 10 cm³ of MeOH. The mixture is agitated at ambient temperature for about 5 hours. The MeOH is driven off under vacuum, dilution is carried out with water and a neutral fraction is extracted with AcOEt. The aqueous phase is filtered off, followed by acidification by the addition of cHCl and extraction with $CHCl_3$ with 20% MeOH then evaporation. The resultant product is impasted in iso ether under agitation, filtered and dried at ambient temperature. In order to carry out purification, 420 mg of the product obtained is dissolved in 50 cm³ of N soda under agitation. A neutral fraction is extracted with ether, the aqueous phase is filtered off and acidification is carried out by slowly adding cHCl under agitation. Agitation is carried out again for about 30 minutes, followed by filtration, washing with water and with essence G and drying. 170 mg of expected product is obtained.

IR Spectrum:

Very complex OH region

| =C—NH | 3400 cm⁻¹ |
|---|---|
| C=O | 1753–1705–1632 cm⁻¹ |
| Aromatic | 1592 cm⁻¹ |
| Heteroaromatic | 1551 cm⁻¹ (F |
| Amide II | 1504 cm⁻¹ |

UV Spectrum:
In EtOH for M=588.75

| | |
|---|---|
| Max. 268 nm | $\epsilon$ = 3100 |
| Max. 276 nm | $\epsilon$ = 2800 |
| Infl. 215, 236 nm | |

EXAMPLE 10
ethyl 2-butyl alpha-hydroxy alpha-methyl 4-(methylthio) 1-[(2'-((((phenylmethyl)amino)carbonyl)amino)sulphonyl)(1,1'-biphenyl)4-yl)methyl]1H-imidazole 5-acetate 500 mg of the product of Example 1 is introduced into 15 cm³ of acetone and 260 mg of potassium carbonate is added. The resultant mixture is heated under reflux and 0.13 cm³ of benzyl isocyanate is introduced. Then reflux is continued for another hour. Filtration is carried out, the solvent is driven off and the residue is purified on silica with $CHCl_3$-MeOH (98-2) as eluant. 590 mg of expected product is recovered.

EXAMPLE 11
2-butyl alpha-hydroxy alpha-methyl 4-(methylthio)1-[(2'-((((phenylmethyl)amino)carbonyl)amino)sulphonyl)(1,1'-biphenyl)4-yl)methyl]1H-imidazole 5-acetic acid 5 cm³ of 2N soda is added to a solution of 590 mg of the product of Example 10 in 10 cm³ of methanol and the mixture is agitated at ambient temperature for about one hour. It is ice-cooled, diluted with water, acidified with cHCl and extraction is carried out with $CHCl_3$ with 20% MeOH. In order to carry out purification, the product obtained is dissolved in 20 cm³ of 2N NaOH and 30 cm³ of water, extraction is carried out with ether, the aqueous solution is filtered off followed by acidification under agitation by the addition of concentrated HCl. Filtration, washing with water then drying are carried out. 444 mg of expected product is obtained. M.p._k=158–160° C.

Microanalysis concordance for $C_{32}H_{36}N_4O_6S_2$=636.79

| | C | H | N | S |
|---|---|---|---|---|
| % calculated | 60.36 | 5.70 | 8.80 | 10.07 |
| % found | 60.2 | 5.5 | 8.6 | 10.2 |

EXAMPLE 12
ethyl 2-butyl 1-[(2'-(((((cyclohexylmethyl)amino)carbonyl)amino)sulphonyl)(1,1'-biphenyl)4-yl)methyl]alpha-hydroxy alpha-methyl 4-(methylthio)1H-imidazole 5-acetate 178 mg of the product of Example 1 is introduced into 10 cm³ of acetone and 46 mg of potassium carbonate is added. The mixture is heated under reflux then 47 mg of cyclohexylmethylisocyanate is introduced. After heating under reflux for about one hour, the insoluble part is filtered off and the solvent is driven off. Purification is carried out on silica with AcOEt-hexane (60-40), then $CHCl_3$-MeOH (95-5) as eluant.

200 mg of expected product is recovered.

EXAMPLE 13
2-butyl 1-[(2'-(((((cyclohexylmethyl)amino)carbonyl)amino)sulphonyl)(1,1'-biphenyl)4-yl)methyl]alpha-hydroxy alpha-methyl 4-(methylthio)1H-imidazole 5-acetic acid 200 mg of the product of Example 12 is introduced into 2 cm³ of ethanol, 0.2 cm³ of 6N KOH is added and the whole is agitated at ambient temperature for about 48 hours. The reaction medium is diluted with water and acidified by the addition of concentrated HCl. Filtration is carried out, followed by washing with water and drying. In order to carry out purification, the residue is dissolved in 60 cm³ of 2N NaOH and 9 cm³ of water. Extraction is carried out with ether, the aqueous phase is filtered off, followed by acidification with concentrated HCl, filtration, washing with water and drying at ambient temperature. 129 mg of expected product is obtained.

Microanalysis for $C_{32}H_{42}N_4O_6S_2$=642.84

| | C | H | N | S |
|---|---|---|---|---|
| % calculated | 59.79 | 6.59 | 8.72 | 9.98 |
| % found | 59.3 | 6.5 | 8.7 | |

EXAMPLE 14
ethyl 1-[(2'-(aminosulphonyl)(1,1'-biphenyl)4-yl)methyl] alpha-hydroxy alpha-2-dimethyl 4-(methylthio)1H-imidazole 5-acetate Stage A
ethyl alpha-hydroxy alpha-2-dimethyl 4-(methylthio)1-[(2'-((((dimethylamino)methylene)amino)sulphonyl)(1,1'-biphenyl)4-yl)methyl]1H-imidazole 5-acetate 1.1 g of the product obtained in Preparation 2 is introduced into 20 cm³ of THF, to which 2.4 cm³ of methyl magnesium chloride is slowly added, agitation is maintained for about one hour at ambient temperature. A saturated solution of $NH_4Cl$ is slowly added to the medium, and after extraction with ethyl acetate, washing with water then drying, purification is carried out on silica with ethyl acetate +5% ethanol as eluant and 770 mg of expected product is obtained.

| IR Spectrum: $CHCl_3$ | |
|---|---|
| OH | 3520 cm⁻¹ |
| C=O | 1725 cm⁻¹ |
| C=N | 1624 cm⁻¹ |
| Aromatic | 1592–1564 cm⁻¹ |
| Heteroaromatic | 1531–1517 cm⁻¹ |

Stage B
ethyl 1-[(2'-(aminosulphonyl)(1,1'-biphenyl)4-yl)methyl] alpha-hydroxy alpha-2-dimethyl 4-(methylthio)1H-imidazole 5-acetate 750 mg of the product obtained in Stage A above is introduced into an ethanol-HCl mixture (20 cm³–5 cm³) and taken to reflux for about 5 hours. Then the medium is concentrated, the resultant product is taken up in ice-cooled water, and alkalinized by the addition of $NH_4OH$, followed by separation, washing with water then drying at ambient temperature. The aqueous phase is extracted with ethyl acetate, washed with water and dried. 540 mg of expected product is recovered in total.

| IR Spectrum: $CHC_3$ Absence of —N=CH— | |
|---|---|
| $NH_2$ | 3445–3440 cm⁻¹ |
| OH | 3515 cm⁻¹ |
| C=O | 1722 cm⁻¹ |
| Aromatic | 1591–1563 cm⁻¹ |
| Heteroaromatic | 1530–1517 cm⁻¹ |
| $NH_2$— def. | |

EXAMPLE 15
N-(phenylmethyl)1-[(2'-(((((phenylmethyl)amino)carbonyl)amino)sulphonyl)(1,1'-biphenyl)4-yl)methyl]alpha-2-dimethyl alpha-hydroxy 4-(methylthio)1H-imidazole 5-acetamide 500 mg of the product of Example 14 is introduced into 20 cm³ of acetone to which 282 mg of potassium carbonate is added and the whole is taken to reflux. 0.15 cm³ of benzyl isocyanate is added. The reaction medium is maintained under agitation and under reflux for about 3 hours. Separation is carried out, followed by washing with ethyl acetate then the organic solution is brought to dryness. First of all purification is carried out on silica with $CH_2Cl_2$-methanol (95-5) as eluant followed by impasting in 20 cm³ of ethanol, separation, washing with 2×5 cm³ of ethanol then drying. The resultant product is dissolved in a mixture of 10 cm³ of ethanol and 10 cm³ of 2N NaOH, then left overnight at ambient temperature. The reaction medium is acidified by the addition of sodium hydrogenphosphate, extraction is carried out with ethyl acetate, the extracts are washed with water then dried. First of all purification is carried out on silica with $CH_2Cl_2$-methanol (90-10) as eluant, then by impasting in 5 cm³ of hot ethanol, separating and washing with 5 cm³ of ethanol. 144 mg of expected product (white solid) is recovered. M.p.=220° C.

IR Spectrum: Nujol
Complex absorptions OH/NH region

| | |
|---|---|
| C=O | 1711–1645 cm⁻¹ |
| Aromatic | 1592–1547 cm⁻¹ |
| Heteroaromatic | 1518–1493 cm⁻¹ |
| Amide II | |

EXAMPLE 16 ethyl alpha-hydroxy alpha-2-dimethyl 4-(methylthio)1-[(2'-(((((phenylmethyl)amino)carbonyl)amino)sulphonyl)(1,1'-biphenyl)4-yl)methyl]1H-imidazole 5-acetate Stage A ethyl 1-[(2'-(aminosulphonyl)(1,1'-biphenyl)4-yl)methyl]2-methyl 4-(methylthio)alpha-oxo 1H-imidazole 5-acetate 4.8 g of the product obtained in Preparation 2 is introduced into a mixture of 50 cm³ of ethanol and 30 cm³ of concentrated HCl. The reaction medium is taken to reflux for about 5 hours. The solution is then concentrated under vacuum then taken up in ice-cooled water. Alkalinization is carried out by the addition of $NH_4OH$a until a pH of about 8 is obtained followed by extraction with ethyl acetate, washing with water, drying then purifying by chromatography on silica with ethyl acetate as eluant.

In this way 2.4 g of expected product is obtained.

IR Spectrum: $CHCl_3$

| | |
|---|---|
| —NH₂ | 3443–3343 cm⁻¹ |
| C=O | 1734–1627 cm⁻¹ |
| Aromatic | 1593 cm⁻¹ |
| Heteroatom | 1565 cm⁻¹ |
| NH₂ def. | 1542 cm⁻¹ |

Stage B ethyl 2-methyl 4-(methylthio)1-[(2'-(((((phenylmethyl)amino)carbonyl)amino)sulphonyl)(1,1'-biphenyl)4-yl)methyl alpha-oxo 1H-imidazole 5-acetate 0.8 g of the product obtained in Stage A above is introduced into 25 cm³ of acetone and 465 mg of potassium carbonate is added. The medium is then taken to reflux, and 0.2 cm³ of benzyl isocyanate is added dropwise, agitation is maintained under these conditions for about one hour. The reaction medium is evaporated to dryness, the residue is taken up in water then acidification is carried out by the addition of sodium hydrogenphosphate, the precipitate is separated off, washed abundantly with water then dried. Purification is carried out by impasting in a mixture of 10 cm³ of isopropanol and 20 cm³ of isopropyl ether, followed by separating, washing with 2×25 cm³ of isopropyl ether and 480 mg of expected product (yellow solid) is obtained.

M.p.=130° C.

IR Spectrum: $CHCl_3$
Absence of $SO_2NH_2$

| | |
|---|---|
| Complex —NH—C= | 3395–3375 cm⁻¹ |
| C=O | 1732–1714–1624 cm⁻¹ broad |
| Aromatic | 1539 cm⁻¹ |
| Heteroatom | 1497 cm⁻¹ |
| Amide II | |

Stage C ethyl alpha-hydroxy alpha-2-dimethyl 4-(methylthio)1-[(2'-(((((phenylmethyl)amino)carbonyl)amino)sulphonyl)(1,1'-biphenyl)4-yl)methyl]1H-imidazole 5-acetate 455 mg of the product obtained in Stage B above is introduced into 10 cm³ of THF, to which 1.25 cm³ of methyl magnesium chloride is added, agitation is maintained for about 30 minutes at ambient temperature, the solution thus obtained is poured into water, extraction is carried out with ethyl acetate, the organic phase is washed with water and dried. Purification is carried out on silica with $CH_2Cl_2$-methanol (95-5) as eluant and 270 mg of expected product is obtained. M.p.=110° C.

IR Spectrum: $CHC_3$

| | |
|---|---|
| —OH | 3515 cm⁻¹ + associated |
| =C—NH | 3395 cm⁻¹ |
| C=O | 1713 cm⁻¹ complex |
| Aromatic | 1605–1592 cm⁻¹ |
| Heteroatom | 1562–1535 cm⁻¹ |
| Amide II | 1498 cm⁻¹ |

EXAMPLE 17 alpha-2-dimethyl alpha-hydroxy 4-(methylthio)1-[(2'-((((((phenylmethyl)amino)carbonyl)amino)sulphonyl)(1,1'-biphenyl)4-yl)methyl]1H-imidazole 5-acetic acid 250 mg of the product of Example 16 is introduced into an NaOH-ethanol mixture (5 cm³–5 cm³) and agitation is maintained for about 3 hours at ambient temperature. The reaction medium is poured into water, then acidification is carried out by the addition of 2N HCl and 20 cm³ of ethyl acetate is added. After about 30 minutes of agitation at about 0° C., the medium is washed abundantly with water, followed by impasting in 2×10 cm³ of boiling ethanol, then in 10 cm³ of isopropyl ether and drying. 165 mg of expected product (white solid) is obtained. M.p.=245° C.

IR Spectrum: $CHCl_3$

| | |
|---|---|
| OH/NH | 3350 cm⁻¹ + general absorption |
| C=O | 1666 cm⁻¹ |
| COO⁻ region | 1625 cm⁻¹ |
| Aromatic | 1607–1580 cm⁻¹ |
| Heteroatom | 1560–1535 cm⁻¹ |
| Amide II | 1497 cm⁻¹ |

EXAMPLE 18 ethyl alpha-hydroxy alpha-2-dimethyl 4-(methylthio)1-[(2'-((((propylamino)carbonyl)amino)sulphonyl)(1,1'-biphenyl)4-yl)methyl]1H-imidazole 5-acetate Stage A
ethyl 2-methyl 4-(methylthio)alpha-oxo 1-[(2'-((((propylamino)carbonyl)amino)sulphonyl)(1,1'-biphenyl)4-yl)methyl]1H-imidazole 5-acetate The process is carried out as in Stage B of Example 16. 0.85 g of the product obtained in Stage A of Example 16 is introduced into 15 cm³ of acetone, to which 500 mg of potassium carbonate is added. The whole is taken to reflux and 0.17 cm³ of n-propyl isocyanate is added then the reaction medium is maintained under reflux for about one hour. The suspension is then concentrated, the residue obtained is taken up in water then acidification is carried out by the addition of 2N hydrochloric acid until a pH of 2 is obtained. Then separation, washing with water and drying at ambient temperature are carried out. The residue is purified on silica with CH₂Cl₂+3% methanol as eluant and 380 mg of expected product is obtained.

| IR Spectrum: CHCl₃ | |
|---|---|
| =C—NH | 3402–3378 cm⁻¹ |
| C=O | 1732–1716–1625 cm⁻¹ |
| COO⁻ region | 1625 cm⁻¹ |
| Aromatic | 1561 cm⁻¹ |
| Amide II | 1540 cm⁻¹ |

Stage B
ethyl alpha-hydroxy alpha-2-dimethyl 4-(methylthio)1-[(2'-((((propylamino)carbonyl)amino)sulphonyl)(1,1'-biphenyl)4-yl)methyl]1H-imidazole 5-acetate The process is carried out as in Stage C of Example 16 starting with 350 mg of the product obtained in Stage A above, in 10 cm³ of THF and 1 cm³ of methyl magnesium chloride is added at a temperature of about 10° C. Then agitation is maintained at ambient temperature for about one hour. A saturated solution of NH₄Cl is then added, followed by extraction with ethyl acetate, washing with water then drying. Purification is carried out on silica with CH₂Cl₂-methanol (95-5) as eluant and 130 mg of expected product is obtained.

EXAMPLE 19
alpha-2-dimethyl alpha-hydroxy 4-(methylthio)1-[(2'-(((((propylamino)carbonyl)amino)sulphonyl)(1,1'-biphenyl)4-yl)methyl]1H-imidazole 5-acetic acid The process is carried out as in Example 17 using 130 mg of the product of Example 18 in 5 cm³ of N NaOH and agitation is maintained at ambient temperature for 16 hours.

The reaction medium is then acidified by the addition of sodium hydrogenphosphate, followed by separation, washing abundantly with water and drying. Purification is carried out by impasting in 5 cm³ of ethyl acetate and 70 mg of expected product is obtained. M.p.=205° C.
IR Spectrum: Nujol
Complex absorptions OH/HN region

| C=O | 1709–1667–1629 cm⁻¹ |
|---|---|
| Aromatic | 1575–1559 cm⁻¹ |
| Amide II | 1550–1513 cm⁻¹ |

EXAMPLE 20
ethyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate
Stage A
ethyl 1-[(2'-(((ethoxycarbonyl)amino)sulphonyl)(1,1'-biphenyl)4-yl)methyl]4-(methylthio)alpha-oxo 2-propyl 1H-imidazole 5-acetate 3.3 g of the product obtained in Preparation 3 is introduced into 60 cm³ of dimethoxyethanol, to which 1.81 g of potassium carbonate then 1.25 cm³ of ethyl chloroformate are added successively. The solution is then taken to reflux for about 5 hours followed by filtration and washing with ethyl acetate and the organic solution is brought to dryness. The residue is taken up in CH₂Cl₂, washed abundantly with water then dried. Purification is carried out by chromatography on silica with CH₂Cl₂-methanol 96-4 as eluant and 1.5 g of expected product is obtained.

| IR Spectrum: CHCl₃ | |
|---|---|
| =C—NH | 3384 cm⁻¹ |
| C=O | 1739–1626 cm⁻¹ |
| Aromatic | 1564 cm⁻¹ |
| Heteroatom | 1516 cm⁻¹ |
| Amide II | 1480 cm⁻¹ |

Stage B
ethyl 1-[(2'-(((ethoxycarbonyl)amino)sulphonyl)(1,1'-biphenyl)4-yl)methyl]alpha-hydroxy 4-(methylthio)2-propyl 1H-imidazole 5-acetate 1.3 g of the product obtained in Stage A above is introduced into 50 cm³ of ethanol, the solution is cooled down to about −20° C./−25° C. and 90 mg of sodium borohydride is added. Agitation is maintained at about −20° C. for about 15 minutes. The ethanol is evaporated off then the residue is taken up in 100 cm³ of ice-cooled water and 50 cm³ of ethyl acetate is added, then the organic phase is evaporated off, followed by separation, washing abundantly then drying. 1.05 g of expected product is obtained. M.p.=147° C.

IR Spectrum: CHCl₃
Absence of conjugated ketone

| OH | 3590–3508 cm⁻¹ |
|---|---|
| —NH | 3385 cm⁻¹ |
| + general absorption | |
| C=O | 1746 cm⁻¹ |
| Aromatic | 1614–1590 cm⁻¹ |
| Heterocycle | 1560–1540 cm⁻¹ |
| Amide | 1538–1500 cm⁻¹ |

Stage C
ethyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate.

1 g of the product obtained in Stage B above is introduced into 30 cm³ of toluene, to which 1 cm³ of benzylamine is added, and the whole is taken to reflux for about 30 minutes. The reaction medium is dried, followed by taking up in water and acidification by the addition of sodium hydrogenphosphate. Extraction is carried out with ethyl acetate, the organic phase is washed with water then dried. Purification is carried out on silica with CH₂Cl₂-ethanol (96-4) as eluant and 730 mg of expected product is obtained.

| IR Spectrum: CHCl₃ | |
|---|---|
| Absorption | |
| OH | 3500 cm⁻¹ |
| NH | 3370 cm⁻¹ complex |
| C=O | 1714 cm⁻¹ |
| Conjugated system | 1664–1592 cm⁻¹ |

-continued

| IR Spectrum: CHCl$_3$ | |
| --- | --- |
| Aromatic | 1538–1502 cm$^{-1}$ |
| Amide II | |

EXAMPLE 21

1-[(2'-(((((phenylmethyl)amino)sulphonyl)(1,1'-biphenyl)4-yl)methyl]alpha-hydroxy 4-(methylthio)2-propyl 1H-imidazole 5-acetic acid 400 mg of the product of Example 20 is introduced into an ethanol-NaOH (5 cm$^3$–5 cm$^3$) mixture and agitation is maintained for about 3 hours at ambient temperature. Then the solution is concentrated, the resultant product is taken up in water and acidified by the addition of N HCl, followed by separation, washing abundantly with water then drying. In order to purify the residue, it is dissolved hot in a mixture of 25 cm$^3$ of ethyl acetate and 25 cm$^3$ of ethanol, followed by filtration, concentration to 50%, then leaving overnight at ambient temperature. After separation, washing the precipitate successively with 20 cm$^3$ of ethyl acetate then 20 cm$^3$ of ethanol and drying, 136 mg of expected product is recovered. M.p.=225° C.

IR Spectrum: CHCl$_3$
Absorption OH/NH C=O 1672–1640 cm$^{-1}$

EXAMPLE 22 ethyl 1-[(2'-(((((cyclohexylmethyl)amino)carbonyl)amino)sulphonyl)(1,1'-biphenyl)4-yl)methyl]4-(methylthio)2-propyl 1H-imidazole 5-carboxylate 400 mg of the product obtained in Preparation 5 is introduced into 5 ml of anhydrous acetone and 236 mg of potassium carbonate K$_2$CO$_3$. The whole is taken to reflux and 200 μl of cyclohexylmethyl isocyanate is added. After about one hour of agitation hot, the solution is cooled down to ambient temperature, hydrolyzed with a saturated aqueous solution of NH$_3$Cl then extraction is carried out with CH$_2$Cl$_2$. After drying and evaporation, recrystallization from ether is carried out after dissolution in the minimum amount of CH$_2$Cl$_2$, followed by filtration and drying and 420 mg of expected product (white solid) is obtained.

| NMR Spectrum: CDCl$_3$ | |
| --- | --- |
| 0.98 (t) | CH$_3$ |
| 1.73 (m) | \| |
| 2.67 (t) | CH$_2$ |
| | \| |
| | CH$_2$-imidazole |
| 0.7 to 1.8 (m) | |
| 2.61 (s) | SMe |
| 2.92 (t, d, after exchange) | NH—CH$_2$ |
| 6.12 (t, mobile) | |
| 1,35 (t); 4.26 (q) | COOEt |
| 6.55 (s) | NCH$_2$ph |
| 7.06 (2H) | |
| 7.35 (2H) | |
| 7.30 (dd) | |
| 7.52 (dt) | |
| 7.62 (dt) | |
| 8.16 (dd) | |

EXAMPLE 23 sodium 1-[(2'-(((((cyclohexylmethyl)amino)carbonyl)amino)sulphonyl)(1,1'-biphenyl)4-yl)methyl]4-(methylthio)2-propyl 1H-imidazole 5-carboxylate 380 mg of the product of Example 22 is introduced into 8 ml of ethanol and 5 ml of 2N NaOH and the solution is left under agitation at ambient temperature for about 48 hours. The ethanol is then evaporated off and after the addition of 10 ml of water, the aqueous phase is extracted with ethyl acetate, then filtered, placed at 0° C. and acidified slowly until a pH of 2 is obtained. After about 30 minutes of agitation, the precipitate is filtered off and dried and 240 mg of expected product is obtained.

IR Spectrum: CHCl$_3$
Acid according to OH region

| =C—NH | 3390 cm$^{-1}$ |
| --- | --- |
| >=O | 1705–1680 cm$^{-1}$ |
| Aromatic | 1606 cm$^{-1}$ |
| Heteroatom | 1545 cm$^{-1}$ |
| Amide II | 1517 cm$^{-1}$ |

EXAMPLE 24 ethyl 4-(methylthio)1-[(2'-(((((phenylmethyl)amino)carbonyl)amino)sulphonyl)(1,1'-biphenyl)4-yl)methyl]2-propyl 1H-imidazole 5-carboxylate 2 g of the product obtained in Preparation 5, dissolved in 25 ml of anhydrous acetone and 1.2 g of potassium carbonate are mixed together. The mixture is taken to reflux and 740 μl of benzylisocyanate is added. After about 2 hours of agitation, the mixture is cooled down to ambient temperature, hydrolyzed with a saturated aqueous solution of NH$_4$Cl then extraction is carried out with methylene chloride. After drying, recrystallization from ether and filtration, 1.9 g of expected product is obtained.

EXAMPLE 25

4-(methylthio)1-[(2'-(((((phenylmethyl)amino)carbonyl)amino)sulphonyl)(1,1'-biphenyl)4-yl)methyl]2-propyl 1H-imidazole 5-carboxylic acid 1.8 g of the product obtained in Example 24 is introduced into 10 ml of ethanol and 10 ml of 2N soda then the whole is left under agitation at ambient temperature for about 36 hours. The ethanol is then evaporated off and, after adding 25 ml of water, the aqueous phase is extracted with ether, then filtered, placed at 0° C. and acidified slowly until a pH of 1.5 is obtained with 1N HCl. After filtration and drying, 1.4 g of expected product is obtained.

IR Spectrum: CHCl$_3$
Acid according to the OH region

| =C—NH | 3480 cm$^{-1}$ |
| --- | --- |
| >=O | 1706–1690 cm$^{-1}$ complex |
| Aromatic | 1539 cm$^{-1}$ |
| Heteroaromatic | 1521 cm$^{-1}$ |
| Amide II | 1500 cm$^{-1}$ |

EXAMPLE 26

4'-((5-acetyl 2-butyl 4-(methylthio)1H-imidazole 1-yl)methyl)N-((propylamino)carbonyl)(1,1'-biphenyl)2-sulphonamide Stage A 4'-((2-butyl 5-((methylsulphinyl)acetyl)4-(methylthio)1H-imidazol 1-yl)methyl)N-((propylamino)carbonyl)(1,1'-biphenyl)2-sulphonamide 3.52 g of NaH at 50% in oil is introduced, the NaH is removed from its oil by 3 successive washings with pentane. Then drying is carried out. 42 cm$^3$ of anhydrous DMSO is added, the mixture is taken to 75° C. for about one hour, then the mixture is cooled down to 0° C. and 40 cm³ of anhydrous THF and dropwise 12 g of ethyl 2-butyl H-(methylthio)1-[[2'-((((propylamino)carbonyl)amino)sulphonyl)( 1,1'-biphenyl)4-yl]methyl]1H-imidazole 5-carboxylate, dissolved in 80 cm³ of anhydrous THF, are added to the anion of the DMSO formed. The resultant product is allowed to rise to ambient temperature and left under agitation for about one hour. Then the reaction mixture is poured into 400 cm³ of distilled water and acidified to a pH of 2, with 2N hydrochloric acid. Extraction is carried out with 3×200 cm³ of methylene chloride and the organic phase is washed with 1×200 cm³ of saturated solution of $NH_4Cl$ and 2×200 cm³ of distilled water.

The organic phase is dried, filtered and concentrated to dryness. It is impasted in isopropyl ether then purified on silica with $CH_2Cl_2$-methanol (95-5) as eluant, followed by impasting in iso ether and 8.93 g of expected product (white powder) is obtained.

| Microanalysis | C | H | N | S | O |
|---|---|---|---|---|---|
| % calculated | 55.61 | 5.99 | 9.27 | 15.9 | 13.23 |
| % found | 55.5 | 5.9 | 9.2 | 16.0 | — |

IR Spectrum: $CHCl_3$

| NH | ~3370 cm⁻¹ associated |
|---|---|
| >=O | 1710–1635 cm⁻¹ |

Stage B
4'-((5-acetyl 2-butyl 4-(methylthio)1H-imidazole 1-yl)methyl)N-((propylamino)carbonyl)(1,1'-biphenyl)2-sulphonamide 20 cm³ of a 10% aqueous solution of ammonium chloride and 650 mg of electrocyclic zinc are added to a solution of 1 g of the product obtained in Stage A above in 35 cm³ of ethanol. The resultant mixture is agitated for 24 hours then filtered, followed by evaporation, redissolving in ethyl acetate, washing with water, drying and evaporation. The residue is purified by passage over silica, eluting with methylene chloride with 2% methanol. 711 mg of expected product is obtained, melting at 176–177° C.

| Microanalysis | C | H | N | S |
|---|---|---|---|---|
| % calculated | 59.75 | 6.31 | 10.32 | 11.82 |
| % found | 59.6 | 6.3 | 10.1 | 11.7 |

IR Spectrum: $CHCl_3$

| NH | 3402 and 3368 cm⁻¹ |
|---|---|
| >=O | 1716 and 1632 cm⁻¹ |
| Aromatic | |
| + heteroaromatic | 1541–1493 cm⁻¹ |
| + Amide II | |

EXAMPLE 27
ethyl 2-butyl 4-(methylthio)1-[(2'-(((((diphenylmethyl)amino)carbonyl)amino)sulphonyl)(1,1'-biphenyl)4-yl)methyl]1H-imidazole 5-carboxylate 1.8 g of ethyl 2-butyl 1-[(2'-(((ethoxycarbonyl)amino)sulphonyl)(1,1'-biphenyl)4-yl)methyl]4-(methylthio)1H-imidazole 5-carboxylate prepared as indicated in EP 0,503, 162 and 1.16 g diphenyl amino methane are dissolved in 70 cm³ of toluene. The resultant mixture is heated for about 14 hours at 85° C., cooled down, AcOEt is added and the organic phase is washed with N HCl, then with water. After drying and evaporating, crystallization from ether is carried out followed by separation and 0.8 g of expected product is obtained. M.p.=125° C.

IR Spectrum: $CHCl_3$

| =C—NH | 3366 cm⁻¹ |
|---|---|
| >=O | 1715–1689–1665 cm⁻¹ |

EXAMPLE 28
potassium 2-butyl 1-[(2'-(((((diphenylmethyl)amino)carbonyl)amino)sulphonyl)(1,1'-biphenyl)4-yl)methyl]4-(methylthio)1H-imidazole 5-carboxylate (double salt of potassium)

7 ml of EtOH 99 is introduced into 350 mg of the product of Example 27 and 0.33 ml of 6N KOH is added dropwise. The whole is agitated for about 48 hours at ambient temperature, followed by separation and washing with 2×2 ml of EtOH 99. The resultant product is impasted in 3.5 cm³ of EtOH 96, followed by agitation for about 45 minutes, separation, washing with 2×1 cm³ of EtOH 96, then with ether. Hot and cold recrystallization from 5 cm³ of EtOH 96 is carried out and 170 mg of expected product is obtained.
M.p.>260° C.
IR Spectrum: Nujol
Complex absorption OH/NH region

| >=O | 1600 cm⁻¹ |
|---|---|
| Aromatic | 1539 cm⁻¹ |
| Heteroatom | 1517 cm⁻¹ |
| | 1494 cm⁻¹ |

Microanalysis for $C_{36}H_{34}K_2N_4O_5S_2H_2$

| | C | R | N | S |
|---|---|---|---|---|
| % calculated | 56.6 | 4.7 | 7.3 | 8.4 |
| % found | 56.0 | 4.7 | 7.2 | 8.5 |

EXAMPLE 29
ethyl 2-butyl 4-(methylthio)1-[(2'-(((diphenylacetyl)amino)sulphonyl)(1,1'-biphenyl)4-yl)methyl]1H-imidazole 5-carboxylate 225 mg of diphenyl acetyl chloride and 119 mg of DMAP are added to a suspension in 10 ml of toluene of 365 mg of ethyl 1-[(2'-(aminosulphonyl)(1,1'-biphenyl)4-yl)methyl]2-butyl 4-(methylthio)1H-imidazole 5-carboxylate, prepared as indicated in EP 0,503,162. The whole is heated to 70° C. for about 30 minutes, cooled down, taken up in water, extraction is carried out with ethyl acetate, followed by drying and evaporating. Crystallization from 5 cm³ of acetonitrile then hot and cold from 7 cm³ of acetonitrile is carried out and 200 mg of expected product is obtained.
M.p.>210° C.
IR Spectrum: $CHCl_3$
Absence of $NH_2$

| NH | 3360 cm⁻¹ + associated |
|---|---|
| C=O | 1725–1680 cm⁻¹ (ester) |
| Aromatic | 1613–1600 cm⁻¹ |
| Heterocycle | 1560–1508 cm⁻¹ |
| Amide II | 1496–1483 cm⁻¹ |

| | |
|---|---|
| SO$_2$ | 1346 cm$^{-1}$ |

EXAMPLE 30
2-butyl 1-[(2'-(((diphenylacetyl)amino)sulphonyl)(1,1'-biphenyl)4-yl)methyl]4-(methylthio)1H-imidazole 5-carboxylic acid 500 mg of the product of Example 29 is dissolved in 10 ml of MeOH and 5 ml of 2N NaOH is added. Agitation is carried out for about 18 hours at ambient temperature, the methanol is evaporated off, the remaining product is taken up in water, extraction is carried out with ethyl acetate, the aqueous phase is acidified with 2N HCl (pH 1) and extraction is carried out with CH$_2$Cl$_2$ followed by drying and evaporating. Hot and cold recrystallization from 50 cm$^3$ of ethanol is carried out and 340 mg of expected product is obtained. M.p.=205° C.

| IR Spectrum: Nujol | |
|---|---|
| OH/NH region: | max 3249 cm$^{-1}$ + general absorption |
| >=O | 1728–1645 cm$^{-1}$ |
| Aromatic + | 1584–1565 cm$^{-1}$ |
| Heteroaromatic | 1545–1510–1495 cm$^{-1}$ |
| UV Spectrum: in EtOH | |
| Max. 284 nm | ε = 14400 |
| Infl. 213,241 | |

EXAMPLE 31
ethyl alpha-butyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate Stage A
ethyl 4-(methylthio)alpha-oxo 1-((2'-(((((phenylmethyl)amino)carbonyl)amino)sulphonyl)(1,1'-biphenyl)4-yl)methyl)2-propyl 1H-imidazole 5-acetate 3.6 g of the product obtained in Preparation 3 is introduced into 50 cm$^3$ of acetone then 2 g of potassium carbonate is introduced in one go. The medium is then taken to reflux and 1 cm$^3$ of benzyl isocyanate is added dropwise to it. Reflux is maintained for 2 hours. Then the medium is poured into 500 cm$^3$ of ice-cooled water, acidified by the addition of N hydrochloric acid, followed by separation, washing abundantly with water and drying at 50° C. The residue is purified by impasting in 50 cm$^3$ of isopropyl ether and 4.2 g of product is obtained 500 mg of which is purified by recrystallization from 25 cm$^3$ of ethanol, and after separation and drying, 300 mg of expected product is obtained. M.p.=188° C.

| IR Spectrum: CHCl$_3$ | |
|---|---|
| =C—NH | 3375 cm$^{-1}$ |
| C=O | 1714–1621 cm$^{-1}$ |
| Conjugated system + | 1537 cm$^{-1}$ |
| Aromatic + | 1495 cm$^{-1}$ |
| Amide II + | |

Stage B
ethyl alpha-butyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate 750 mg of the product obtained in Stage A above is introduced into 50 cm$^3$ of anhydrous THF, the mixture is cooled down to 0° C. and 2.8 cm$^3$ of n-butyl magnesium chloride is added dropwise, agitation is maintained at 0° C. for 30 minutes then at ambient temperature for one hour. The reaction medium is acidified by the addition of 0.1 N hydrochloric acid, then extraction is carried out with ethyl acetate. The organic phase is washed abundantly with water then dried. A yellow resin is recovered. It is purified by 2 successive chromatographies on silica with CH$_2$Cl$_2$+2.5% methanol as eluant and 300 mg of expected product is obtained.

| IR Spectrum: CHCl$_3$ | |
|---|---|
| OH | 3520 cm$^{-1}$ |
| NH | 3408 cm$^{-1}$ |
| C=O | 1714 cm$^{-1}$ |
| Conjugated system | 1604 cm$^{-1}$ |
| Aromatic | 1532 cm$^{-1}$ (complex, F) |
| Amide II | 1500 cm$^{-1}$ |

EXAMPLE 32
sodium alpha-butyl alpha-hydroxy 4-(methylthio)1-[(2'-(((((phenylmethyl)amino)carbonyl)amino)sulphonyl)(1,1'-biphenyl)4-yl)methyl]2-propyl 1H-imidazole 5-acetate 260 mg of the product obtained in Example 31 is introduced into 5 cm$^3$ of soda and 20 cm$^3$ of ethanol, agitation is maintained for 4 hours at ambient temperature. The reaction medium is acidified by the addition of 2N HCl, after extraction with ethyl acetate, washing the organic phase with water then drying, purification is carried out by chromatography on silica with CH$_2$Cl$_2$-methanol as eluant. Another purification is carried out by HPLC on silica with H$_2$O-methanol (60-40) as eluant and 90 mg of expected product is obtained. M.p.=210° C.

IR Spectrum: Nujol
Complex absorption OH/NH region

| | |
|---|---|
| C=O | 1610 cm$^{-1}$ (F) |
| Aromatic | 1520 cm$^{-1}$ |
| Heteroatom | 1500 cm$^{-1}$ |
| Amide II | |

EXAMPLE 33
4'-[(5-(1,2-dihydroxyethyl)4-(methylthio)2-propyl 1H-imidazole 1-yl)methyl)N-(((phenylmethyl)amino)carbonyl)(1,1'-biphenyl)2-sulphonamide 500 mg of the product obtained in Stage A of Example 31 is dissolved in 10 cm$^3$ of THF. The solution is cooled down to 0° C. and 2 ml of LibH$_4$ in 2M/THF solution is added. After 3 hours at ambient temperature, 2 cm$^3$ of acetic acid, 20 cm$^3$ of H$_2$O are added and extraction is carried out with AcOEt. The extracts are dried and evaporate to dryness. After chromatography on silica, eluant: CH$_2$Cl$_2$/MeOH (94/6) and impasting in isopropyl ether, 75 mg of expected product is recovered. M.p.=140° C.

EXAMPLE 34
alpha-hydroxy 4-(methylthio)alpha-phenyl 1-((2'-(((((phenylmethyl)amino)carbonyl)amino)sulphonyl)(1,1'-biphenyl)4-yl)methyl)2-propyl 1H-imidazole 5-acetic acid 250 mg of the product obtained in Stage A of Example 31 is dissolved in 5 cm$^3$ of anhydrous THF. 430 μl of 3M PhMgBr in ether is added dropwise. After one hour at ambient temperature, the reaction medium is hydrolyzed with 2N HCl, extraction is carried out with AcOEt, followed by drying and evaporating to dryness.

The crude product obtained is dissolved in a mixture of 5 cm³ of ethanol and 5 cm³ of 2N NaOH. After one night at ambient temperature, acidification is carried out with 1N HCl, followed by filtration, washing the precipitate obtained with water then with 5 cm³ of AcOEt and 5 cm³ of isopropyl ether. 67 mg of a white solid is obtained. M.p.=170° C.

EXAMPLE 35
2-butyl 4-(methylthio)1-((2'-((((propylamino)carbonyl) amino)sulphonyl)(1,1'-biphenyl)4-yl)methyl)1H-imidazole 5-carboxamide 600 mg of 2-butyl H-(methylthio)1-[[2'-((((propylamino) carbonyl)amino)sulphonyl)( 1,1'-biphenyl)4-yl]methyl]1H-imidazole 5-carboxylic acid is introduced into 15 ml of toluene and 600 µl of thionyl chloride $SOCl_2$ is added. The whole is agitated for about one hour at ambient temperature, then overnight at about 55° C. The solvent is then evaporated off, the remaining product is taken up in toluene and evaporation is carried out again. After drying and taking up in 15 ml of dioxane, 10 drops of $NH_4OH$ (at 20%) are added. After about one hour of agitation, the reaction medium is acidified to a pH of 4 with 1N HCl, then extraction is carried out with $CH_2Cl_2$ followed by drying. Purification is carried out on silica with $CH_2Cl_2$-AcOEt (50-50), then AcOEt-$CH_2Cl_2$-MeOH (50-50-5%) as eluant and after evaporation, 350 mg of expected product (white solid) is obtained.

| IR Spectrum: CHCl₃ | |
|---|---|
| =C—NH₂ | 3383–3375 cm⁻¹ |
| =C—NH | 3315 cm⁻¹ |
| >=O | 1710–1651 cm⁻¹ |
| Aromatic | 1616 cm⁻¹ |
| Heteroaromatic | 1584 cm⁻¹ |
| Amide II | 1545 cm⁻¹ |
| NH₂ | 1506 cm⁻¹ |

Microanalysis: $C_{26}H_{33}N_5O_4S_2$ M=543

| | C | H | N | S |
|---|---|---|---|---|
| % calculated | 57.4 | 6.12 | 12.87 | 11.79 |
| % found | 57.6 | 6.0 | 12.4 | 11.6 |

The following products were prepared according to the process described in Example 23 or 25 starting with suitable compounds.

EXAMPLE 36
4-bromo 1-((2'-(((((phenylmethyl)amino)carbonyl)amino) sulphonyl)(1,1'-biphenyl)4-yl)methyl)2-propyl 1H-imidazole 5-carboxylic acid M.p.=128° C. Rf=0.34 (MeOH-$CH_2Cl_2$ 20-80).

EXAMPLE 37
4-bromo alpha-hydroxy alpha-methyl 1-((2'-(((((phenylmethyl)amino)carbonyl)amino)sulphonyl)(1,1'-biphenyl)4-yl)methyl)2-propyl 1H-imidazole 5-acetic acid M.p.=153° C. Rf=0.46 (MeOH-$CH_2Cl_2$ 20-80).

EXAMPLE 38
4-(butylthio)alpha-oxo 1-((2'-(((((phenylmethyl)amino) carbonyl)amino)sulphonyl)( 1,1'-biphenyl)4-yl)methyl)2-propyl 1H-imidazole 5-acetic acid M.p.=192° C. Rf=0.36 (MeOH-$CH_2Cl_2$ 20-80).

EXAMPLE 39
4-(butylthio)1-((2'-(((((phenylmethyl)amino)carbonyl) amino)sulphonyl)(1,1'-biphenyl)4-yl)methyl)2-propyl 1H-imidazole 5-carboxylic acid M.p.=197° C.

EXAMPLE 40
1-((2'-(((3-cyclopentyl 1-oxopropyl)amino)sulphonyl (1,1'-biphenyl)4-yl)methyl)4-(methylthio)2-propyl 1H-imidazole 5-carboxylic acid M.p.≃190° C. Rf=0.4 ($CH_2Cl_2$-MeOH 95-5).

EXAMPLE 41
alpha-hydroxy alpha-methyl 4-(methylthio)1-((2'-(((((phenylmethyl)amino)carbonyl)amino)sulphonyl (1,1'-biphenyl)4-yl)methyl)2-propyl 1H-imidazole 5-acetamide acid M.p.=213–215° C. Rf=0.25 ($CH_2Cl_2$-MeOH 9-1).

EXAMPLE 42
2-butyl 4-(methylthio)1-(2'-(((phenylacetyl)amino) sulphonyl)(1,1'-biphenyl)4-yl)methyl)1H-imidazole 5-carboxylic acid M.p.≃175° C.

EXAMPLE 43
2-butyl alpha-hydroxy alpha-methyl 4-(methylthio)1-((2'-(((phenylacetyl)amino)sulphonyl) (1,1'-biphenyl)4-yl) methyl)5-imidazolacetic acid Rf=0.4 (AcOEt-EtOH-$H_2O$ 70-20-10).

EXAMPLE 44
2-ethyl 4-(methylthio)1-((2'-(((((phenylmethyl)amino) carbonyl)amino)sulphonyl)(1,1'-biphenyl)4-yl)methyl)1H-imidazole 5-carboxylic acid M.p.=164° C. Rf # 0.6 (AcOEt-EtOH-$H_2O$ 70-20-10).

EXAMPLE 45
1-((2'-(((((cyclohexylmethyl)amino)carbonyl)amino) sulphonyl)(1,1'-biphenyl 4-yl)methyl)4-(difluoromethyl) thio)2-propyl 1H-imidazole 5-carboxylic acid M.p.=125° C. Rf=0.1 ($CH_2Cl_2$-MeOH 95-5).

EXAMPLE 46
4-((difluoromethyl)thio)1-((2'-(((((phenylmethyl)amino) carbonyl)amino)sulphonyl)(1,1'-biphenyl)4-yl)methyl)2-propyl 1H-imidazole 5-carboxylic acid M.p.=150° C. Rf=0.1 ($CH_2Cl_2$-MeOH 95-5).

EXAMPLE 47
4-((difluoromethyl)thio)2-propyl 1-(2'-(((((2-thien- 2-yl-ethyl)amino)carbonyl)amino)sulphonyl)(1,1'-biphenyl)4-yl) methyl)1H-imidazole 5-carboxylic acid M.p.=130° C. Rf=0.1 ($CH_2Cl_2$-MeOH 95-5).

EXAMPLE 48
4-((difluoromethyl)thio)1-(2'-(((((2-phenylethyl)amino) carbonyl)amino)sulphonyl)(1,1'-biphenyl)4-yl)methyl)2-propyl 1H-imidazole 5-carboxylic acid M.p.=118 C. Rf=0.1 ($CH_2Cl_2$-MeOH 95-5).

EXAMPLE 49
1-((2'-(((((2-chlorophenylmethyl)amino)carbonyl)amino) sulphonyl)(1,1'-biphenyl)4-yl)methyl)4-((difluoromethyl) thio)2-propyl 1H-imidazole 5-carboxylic acid M.p.=134° C. Rf=0.1 ($CH_2Cl_2$-MeOH 95-5).

EXAMPLE 50
4-((difluoromethyl)thio)2-propyl 1-((2'-(((((2-thienylmethyl)amino)carbonyl)amino)sulphonyl)(1,1'-biphenyl)4-yl)methyl)1H-imidazole 5-carboxylic acid M.p.=142° C. Rf=0.1 ($CH_2Cl_2$-MeOH 95-5).

EXAMPLE 51
1-((2'-(((((1,3-benzodioxol 5-yl)methyl)amino)carbonyl) amino)sulphonyl)(1,1'-biphenyl 4-yl)methyl)4-((difluoromethyl)thio)2-propyl 1H-imidazole 5-carboxylic acid M.p.=124° C. Rf=0.1 (CH$_2$Cl$_2$-MeOH 95-5).

EXAMPLE 52
4-((difluoromethyl)thio)1-((2'-(((((1-naphthylmethyl) amino)carbonyl)amino)sulphonyl)(1,1'-biphenyl)4-yl) methyl)2-propyl 1H-imidazole 5-carboxylic acid M.p.=144° C. Rf=0.1 (CH$_2$Cl$_2$-MeOH 95-5).

EXAMPLE 53
4-((difluoromethyl)thio)1-((2'-(((((3-phenylpropyl)amino) carbonyl)amino)sulphonyl)(1,1'-biphenyl)4-yl)methyl)2-propyl 1H-imidazole 5-carboxylic acid M.p.=108° C. Rf=0.1 (CH$_2$Cl$_2$-MeOH 95-5).

EXAMPLE 54
1-((2'-((((2-cyclopentylethyl)carbonyl)amino)sulphonyl)(1, 1'-biphenyl 4-yl)methyl)4-((difluoromethyl)thio)2-propyl 1H-imidazole 5-carboxylic acid M.p.=118° C. Rf=0.2 (CH$_2$Cl$_2$-MeOH 95-5).

EXAMPLE 55
4-((difluoromethyl)thio)1-((2'-(((((4-fluorophenylmethyl) amino)carbonyl)amino)sulphonyl)(1,1'-biphenyl) 4-yl) methyl)2-propyl 1H-imidazole 5-carboxylic acid M.p.=122° C. Rf=0.1 (CH$_2$Cl$_2$-MeOH 95-5).

EXAMPLE 56
1-((2'-(((((2-cyclohexen-1-yl-ethyl)amino)carbonyl)amino) sulphonyl)(1,1'-biphenyl)4-yl)methyl)4-((difluoromethyl) thio)2-propyl 1H-imidazole 5-carboxylic acid M.p.=114° C. Rf=0.1 (CH$_2$Cl$_2$-MeOH 95-5).

EXAMPLE 57
4-(methylthio)1-((2'-((((((1-phenylethyl)amino)carbonyl) amino)sulphonyl)(1,1'-biphenyl)4-yl)methyl)2-propyl 1H-imidazole 5-carboxylic acid M.p.=139° C. Rf=0.15 (CH$_2$Cl$_2$-MeOH 95-5).

EXAMPLE 58
1-((2'-((((cyclohexylamino)carbonyl)amino)sulphonyl)(1, 1'-biphenyl 4-yl)methyl)4-(methylthio)2-propyl 1H-imidazole 5-carboxylic acid M.p.=150° C. Rf=0.1 (CH$_2$Cl$_2$-MeOH 95-5).

EXAMPLE 59
2-butyl 4-chloro 1-((2'-(((((phenylmethyl)amino)carbonyl) amino)sulphonyl)(1,1'-biphenyl 4-yl)methyl)1H-imidazole 5-carboxylic acid M.p.≃135° C.

EXAMPLE 60
2-butyl 4-((difluoromethyl)thio)1-((2'-(((((phenylmethyl) amino)carbonyl)amino)sulphonyl)(1,1'-biphenyl)4-yl) methyl)1H-imidazole 5-carboxylic acid Rf=0.4 (CH$_2$Cl$_2$-MeOH 90-10).

EXAMPLE 61
2-butyl 1-((2'(((((cyclohexylmethyl)amino)carbonyl)amino) sulphonyl)(1,1'-biphenyl)4-yl)methyl)4-((difluoromethyl) thio)1H-imidazole 5-carboxylic acid M.p.=130 C.

EXAMPLE 62
4-(methylthio)1-((2'-((((phenylamino)carbonyl)amino) sulphonyl)(1,1'-biphenyl)4-yl)methyl)2-propyl 1H-imidazole 5-carboxylic acid Rf=0.55 (AcOEt-EtOH-H$_2$O 70-20-10).

EXAMPLE 63
1-((2'-(((((4-methylphenyl)amino)carbonyl)amino) sulphonyl)(1,1'-biphenyl)4-yl)methyl)4-(methylthio)2-propyl 1H-imidazole 5-carboxylic acid Rf=0.70 (AcOEt-EtOH-H$_2$O 70-20-10).

EXAMPLE 64
2-ethyl alpha-hydroxy 4-(methylthio)alphaphenyl 1-((2'-(((((phenylmethyl)amino)carbonyl)amino)sulphonyl)( 1,1'-biphenyl)4-yl)methyl)1H-imidazole 5-acetic acid M.p.≃200° C. (decomp.). Rf # 0.25 (CH$_2$Cl$_2$-MeOH 90-10).

EXAMPLE 65
2-butyl beta-hydroxy 4-(methylthio)1-((2'-(((((phenylmethyl)amino)carbonyl)amino)sulphonyl)(1,1'-biphenyl)4-yl)methyl)1H-imidazole 5-propionic acid M.p.≃190° C. Rf # 0.1 (CH$_2$Cl$_2$-MeOH 90-10).

EXAMPLE 66
1-((2'-(((butoxycarbonyl)amino)sulphonyl)(1,1'-biphenyl)4-yl)methyl)4-(methylthio)2-propyl 1H-imidazole 5-carboxylic acid M.p.=202–204° C. Rf=0.30 (CHCl$_3$-MeOH 90-10).

EXAMPLE 67
4-(methylthio)2-propyl 1-((2'-(((((2-thienylmethyl)amino) carbonyl)amino)sulphonyl)(1,1'-biphenyl)4-yl)methyl)1H-imidazole 5-carboxylic acid M.p.≃140° C. Rf=0.1 (CH$_2$Cl$_2$-MeOH 95-5).

EXAMPLE 68
1-((2'-(((((cyclopentylmethyl)amino)carbonyl)amino) sulphonyl)(1,1'-biphenyl)4-yl)methyl)4-(methylthio)2-propyl 1H-imidazole 5-carboxylic acid M.p.≃190° C. Rf=0.4 (CH$_2$Cl$_2$-MeOH 90-10).

By operating in an identical manner to Example 28, the following was prepared:

EXAMPLE 69
potassium 1-((2'-(((((cyclohexylmethyl)amino)carbonyl) amino)sulphonyl)(1,1'-biphenyl 4-yl)methyl)2-ethyl 4-(methylthio)1H-imidazole 5-carboxylate (potassium salt)

M.p.>260° C. Rf # 0.33 (CH$_2$Cl$_2$-MeOH 90-10).

By operating as in Example 5 starting with the acid or the ester and the appropriate isocyanate, the following were prepared:

EXAMPLE 70
4'-((5-formyl 4-(methylthio)2-propyl 1H-imidazol-1-yl) methyl)N-(((phenylmethyl)amino)carbonyl)(1,1'-biphenyl) 2-sulphonamide M.p.=180° C. Rf=0.3 (CH$_2$Cl$_2$-AcOEt 70-30).

EXAMPLE 71
2-butyl 1-((2'-(((((cyclohexylmethyl)amino)carbonyl) amino)sulphonyl)(1,1'-biphenyl)4-yl)methyl)alpha-hydroxy 4-(methylthio)alpha-(trifluoromethyl)1H-imidazole 5-acetic acid Rf=0.45 (AcOEt-EtOH-H$_2$O 70-20-10).

EXAMPLE 72
2-butyl alpha-hydroxy 4-(methylthio)1-((2'-(((((phenylmethyl)amino)carbonyl)amino)sulphonyl)(1,1'-biphenyl)4-yl)methyl)alpha-(trifluoromethyl)1H-imidazole 5-acetic acid Rf=0.60 (AcOEt-EtOH-H$_2$O 70-20-10).

EXAMPLE 73
2-butyl 4-(methylthio)1-((2'-(((((phenylamino)carbonyl)amino)sulphonyl)(1,1'-biphenyl)4-yl)methyl)1H-imidazole 5-carboxylic acid M.p.≃165° C. Rf # 0.65 (AcOEt-EtOH-H$_2$O 70-20-10).

EXAMPLE 74
2-butyl alpha-hydroxy 5-(methylthio)1-((2'-(((((phenylmethyl)amino)carbonyl)amino)sulphonyl)(1,1'-biphenyl)4-yl)methyl)alpha-(trifluoromethyl)1H-imidazole 4-acetic acid Rf=0.25 (AcOEt-EtOH-H$_2$O 70-20-10).

EXAMPLE 75
2-butyl 1-((2'-(((((cyclohexylmethyl)amino)carbonyl)amino)sulphonyl)(1,1'-biphenyl)4-yl)methyl)4-(methylthio)1H-imidazole 5-carboxylic acid M.p.≃175° C. Rf # 0.6 (CH$_2$Cl$_2$-MeOH 80-20).

EXAMPLE 76
ethyl 1-((2'-(((((cyclohexylmethyl)amino)carbonyl)amino)sulphonyl)(1,1'-biphenyl)4-yl)methyl)4-(methylthio)2-propyl 1H-imidazole 5-carboxylate M.p.≃104° C. Rf=0.30 (CHCl$_3$-MeOH 80-20).

By operating as in Example 26 starting with the appropriate ester and chloroformate, the following was prepared:

EXAMPLE 77
ethyl 1-((2'-(((butoxycarbonyl)amino)sulphonyl)(1,1'-biphenyl)4-yl)methyl)4-(methylthio)2-propyl 1H-imidazole 5-carboxylate Rf=0.40 (AcOEt-Hexane 60-40).

By operating as in Example 20 Stage B, starting with the appropriate derivative, the following were prepared:

EXAMPLE 78
4'-((2-butyl 5-(alpha-hydroxy (1H-tetrazolyl)methyl)4-(methylthio)1H-imidazol-1-yl)methyl)N-(((phenylmethyl)amino)carbonyl)(1,1'-biphenyl)2-sulphonamide, sodium derivative M.p.=180° C. Rf=0.2 (CH$_2$Cl$_2$-MeOH 80-20).

EXAMPLE 79
ethyl 3-(2-butyl 1-((2'-(((propylamino)carbonyl)amino)sulphonyl)(1,1'-biphenyl)4-yl)methyl)4-(methylthio)1H-imidazol-5-yl)3-hydroxy propanoate M.p.=135–136° C.

By operating as in Example 31 Stage B or Example 34 using the appropriate magnesium compound and ester, the following were prepared:

EXAMPLE 80
sodium alpha-ethyl alpha-hydroxy 4-(methylthio)1-((2'-(((((phenylmethyl)amino)carbonyl)amino)sulphonyl)(1,1'-biphenyl)4-yl)methyl)2-propyl 1H-imidazole 5-acetate (sodium salt)

M.p.=215° C. Rf=0.35 (CH$_2$Cl$_2$-MeOH 90-10).

EXAMPLE 81
sodium alpha-hydroxy alpha-hexyl 4-(methylthio)1-((2'-(((((phenylmethyl)amino)carbonyl)amino)sulphonyl)(1,1'-biphenyl)4-yl)methyl)1H-imidazole 5-acetate (sodium salt)

M.p.≃190° C. Rf=0.35 (CH$_2$Cl$_2$-MeOH 90-10).

EXAMPLE 82
sodium alpha-hydroxy 4-(methylthio)alpha-(phenylmethyl)1-((2'-(((((phenylmethyl)amino)carbonyl)amino)sulphonyl)(1,1'-biphenyl)4-yl)methyl)2-propyl 1H-imidazole 5-acetate (sodium salt)

M.p.=220° C. Rf=0.3 (CH$_2$Cl$_2$-MeOH 90-10).

EXAMPLE 83
alpha-hydroxy alpha-(1-methylethyl)4-(methylthio)1-((2'-(((((phenylmethyl)amino)carbonyl)amino)sulphonyl)(1,1'-biphenyl)4-yl)methyl)2-propyl 1H-imidazole 5-acetic acid M.p.=180° C. Rf=0.36 (CH$_2$Cl$_2$-MeOH 90-10).

EXAMPLE 84
alpha-ethenyl alpha-hydroxy 4-(methylthio)1-((2'-(((((phenylmethyl)amino)carbonyl)amino)sulphonyl)(1,1'-biphenyl)4-yl)methyl)2-propyl 1H-imidazole 5-acetic acid M.p.=225° C. Rf=0.15 (CH$_2$Cl$_2$-MeOH 90-10).

By heating the appropriate carbamate with cyclopentyl-methylamine in toluene at 100° C., the following was prepared:

EXAMPLE 85
ethyl 1-((2'-(((((cyclopentylmethyl)amino)carbonyl)amino)sulphonyl)(1,1'-biphenyl)4-yl)methyl)4-(methylthio)2-propyl 1H-imidazole 5-carboxylate M.p.≃163° C. Rf=0.5 (CH$_2$Cl$_2$-AcOEt 80-20).

By hydrogenating the appropriate derivative in methanol for 2 hours at 50° C. under a pressure of 2 bars in the presence of a catalyst, the following was prepared:

EXAMPLE 86
2-butyl alpha-methyl 4-(methylthio)1-((2'-(((((phenylmethyl)amino)carbonyl)amino)sulphonyl)(1,1'-biphenyl)4-yl)methyl)1H-imidazole 5-acetic acid Rf=0.30 (CHCl$_3$-MeOH 90-10).

EXAMPLE 87
of pharmaceutical composition.

Tablets were prepared corresponding to the following formula:

| Product of Example 15 | 50 mg |
| --- | --- |
| Excipient for a tablet made up to | 200 mg |

(detail of the excipient: lactose, talc, starch, magnesium stearate).

PHARMACOLOGICAL RESULTS

1-Test on the AT$_1$ receptor of angiotensin II

A fresh membrane preparation obtained from rat's liver is used. The tissue is ground up in a polytron in a 50 mM Tris buffer pH 7.4, the grinding is followed by 3 centrifugations at 30,000 g for 15 minutes with intermediate take up of the pellets in the Tris buffer pH 7.4.

The last pellets are suspended in an incubation buffer (20 mM Tris, 135 mM NaCl, 10 mM KCl, 5 mM glucose, 135 mM MgCl$_2$, 0.3 mM PMSF, 0.1 mM bacitracin, 0.1% lysozyme).

1 ml aliquoted fractions are distributed in glass tubes and $^{125}$I angiotensin II (25,000 DPM/tube) and the product being studied are added. (The product is first tested with $3 \times 10^{-5}$M three times). When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined).

The non-specific bond is determined by the addition of the product of Example 94 of the European Patent 0,253,310, at $10^{-5}$M (three times). After incubation at 25° C. for 150 minutes, placing in a water-bath at 0° C. for 5 minutes, filtration under vacuum, and rinsing with Tris buffer pH 7.4, the radioactivity is counted in the presence of a scintillating solid.

The result is expressed directly as the 50% inhibitory concentration ($IC_{50}$), that is to say as the concentration of product studied, expressed in nM, necessary to displace by 50% the specific radioactivity fixed to the receptor studied.

Results:

| Product of Example | $AT_1$ Receptor $IC_{50}$ in nanomoles |
|---|---|
| 7 | 0.7 |
| 9 | 3.4 |
| 11 | 24 |
| 13 | 6.3 |
| 21 | 2.5 |
| 23 | 0.2 |
| 25 | 0.2 |
| 32 | 0.5 |
| 34 | 0.7 |
| 44 | 0.06 |
| 45 | 0.07 |
| 46 | 0.11 |
| 47 | 0.03 |
| 50 | 0.06 |
| 59 | 0.08 |
| 75 | 0.05 |

2) Test on the $AT_2$ receptor of angiotensin II

A fresh membrane preparation obtained from rabbit's uterus is used, which has been pre-treated 4 days beforehand with 50 μg of estradiol administered by percutaneous route. The tissue is ground up in a polytron in a 50 mM Tris buffer pH 7.4, and the grinding is followed by 3 centrifugations at 30,000 g for 15 minutes, with intermediate take up of the pellets in the Tris buffer pH 7.4.

The last pellets are suspended in an incubation buffer (20 mM Tris, 135 mM NaCl, 10 mM KCl, 5 mM glucose, 10 mM $MgCl_2$, $6H_2O$, 0.3 mM PMSF, 0.1 mM bacitracin, 0.1% lysozyme, pH 7.4).

The homogenate obtained is preincubated for 20 minutes at 25° C. in the presence of 10 mM dithiothreitol, then brought back to 0°–4° C.

1 ml aliquoted fractions are distributed in glass tubes and $^{125}$I angiotensin II (25,000 DPM/tube) and the product being studied are added. The product is first tested at $3.10^{-5}$M three times. When the tested product displaces more than 50% of the radioactivity specifically bound to the receptor, it is tested again according to a range of 7 concentrations in order to determine the concentration which inhibits by 50% the radioactivity specifically bound to the receptor. In this way the 50% inhibitory concentration is determined.

The specific bond is determined by the addition of EXP 655 (=PD 123–177 from Warner-Lamber) at $10^{-5}$M three times. After incubation at 25° C. for 150 minutes, placing in a water-bath at 0° C. for 5 minutes, filtration under vacuum, and rinsing with Tris buffer pH 7.4, the radioactivity is counted in the presence of a scintillating solid.

The result is expressed directly as the 50% inhibitory concentration ($IC_{50}$), that is to say as the concentration of product studied, expressed in nM, necessary to displace by 50% the specific radioactivity fixed to the receptor studied.

Results:

| Product of Example | $AT_2$ Receptor $IC_{50}$ in nanomoles |
|---|---|
| 7 | 5.2 |
| 9 | 8.5 |
| 11 | 1.6 |
| 13 | 1.9 |
| 21 | 6.5 |
| 23 | 2.0 |
| 25 | 5.9 |
| 32 | 0.8 |
| 34 | 2.1 |
| 45 | 1.7 |
| 46 | 0.26 |
| 50 | 7.4 |
| 54 | 2.1 |
| 56 | 5.8 |
| 63 | 3.5 |
| 69 | 1.3 |

The following results are also in particular obtained for products P1 to P13 mentioned above:

| PRODUCT | On $AT_1$ receptor $IC_{50}$ | On $AT_2$ receptor $IC_{50}$ |
|---|---|---|
| P1 | 0.23 | 17 |
| P2 | 0.10 | 14 |
| P3 | 1.1 | 11 |
| P4 | 0.5 | 47 |
| P5 | 0.3 | 25 |
| P6 | 0.27 | 10 |
| P7 | 0.4 | 49 |
| P8 | 0.14 | 17 |
| P9 | 0.19 | 53 |
| P10 | 0.7 | 31 |
| P11 | 0.14 | 24 |
| P12 | 0.8 | 54 |
| P13 | 5.9 | 63 |

3-Test for antagonistic activity of angiotensin II in the demedullated rat

Male Sprague-Dawley rats (250 to 350 g) are anaesthetized by an intraperitoneal injection with sodium pentobarbital (60 mg/kg). The diastolic arterial pressure is recorded by means of a heparin catheter (PE50) introduced into the left carotid of the animal, and connected to a pressure processor (Gould, Pressure Processor) via a Gould pressure sensor.

A catheter is introduced into the right jugular vein of the animal in order to allow injection of the molecules being studied.

The animal is placed under assisted respiration. A bilateral section of the vagus nerves is carried out. The rat is then demedullated.

After a sufficient stabilization period, study of the antagonism of the molecules vis-à-vis angiotensin II (Hypertensin, CIBA) is carried out in the following manner:

1-Three consecutive injections of angiotensin II (0.75 micrograms/kg) 15 minutes apart allow a reproducible and stable pressure response to be obtained.

2-While maintaining a periodicity of 15 minutes for the administration of angiotensin II, the molecules (0.01 to 10 mg/kg) are injected 5 minutes before the angiotensin II. The pressure effects of angiotensin II in the presence of the antagonist are expressed as a percentage of the pressure effects of angiotensin II administered alone. The 50% inhibitory dose ($ID_{50}$) of the effect studied is thus determined. Each animal is considered as its own control.

Results:

| Product of Example | $ID_{50}$ in mg/kg | |
| --- | --- | --- |
|  | IV | PO |
| 7 | 0.6 | — |
| 23 | 0.3 | 1.54 |
| 25 | 0.22 | 1.45 |
| 30 | 0.93 | — |
| 32 | 0.46 | — |
| 35 | 0.05 | — |
| 45 | 0.22 | 1.1 |
| 46 | 0.26 | 2 |
| 47 | 0.33 | 3 |
| 48 | 0.64 | — |
| 50 | 0.13 | — |
| 62 | 0.52 | — |
| 65 | 0.05 | — |
| 75 | 0.35 | — |

We claim:

1. A compound selected from the group consisting of all possible racemic, enantiomeric and diastero-isomeric forms of a compound of the formula

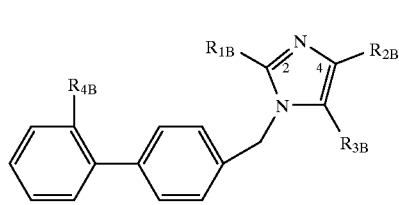

(I$_B$)

wherein $R_{1B}$ is alkyl of 1 to 4 carbon atoms, $R_{2B}$ is alkylthio of 1 to 4 carbon atoms unsubstituted or substituted with at least one fluorine, $R_{3B}$ is carboxy amidified with —NH$_2$ or mono- and dialkylamino, $R_{4B}$ is selected from the group consisting of —SO$_2$NH$_2$, —SO$_2$N=CH—N(CH$_3$)$_2$,

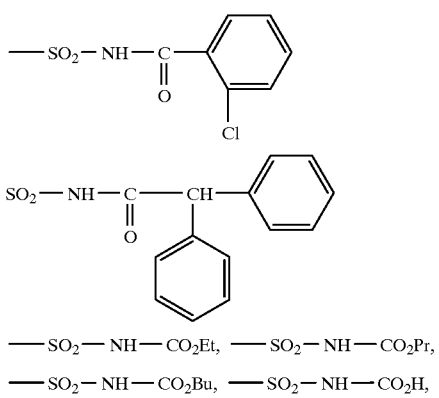

—SO$_2$—NH—CO$_2$Et, —SO$_2$—NH—CO$_2$Pr,
—SO$_2$—NH—CO$_2$Bu, —SO$_2$—NH—CO$_2$H,

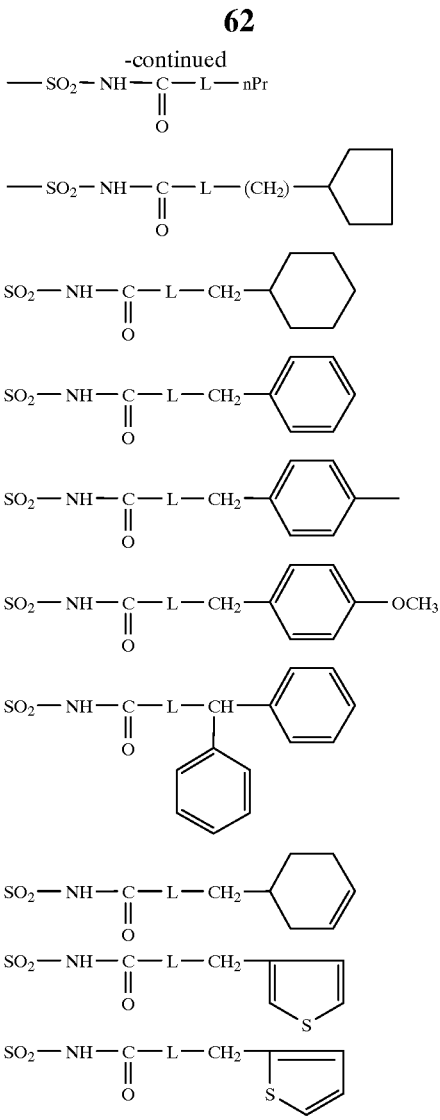

and L is —O— or —NH—, with sulfur atoms being oxidized to sulfone or sulfoxide and its non-toxic, pharmaceutically acceptable addition salts with acids and bases.

2. A compound of claim 1 which is 2-butyl-4-methylthio-1-[(2'-(((propylamino)-carbonyl-amino)-sulfonyl)-(1,1'-biphenyl)-4-yl)-methyl]-1H-imidazole-5-carboxamide.

3. An angiotensin II inhibitory composition comprising an angiotensin II inhibitory effective amount of a compound of claim 1 and an inert carrier.

4. A method of treating renal insufficiency in warm-blooded animals comprising administering to warm-blooded animals in need thereof an amount of claim 1 sufficient to treat renal insufficiency.

5. A method of treating cardiovascular disorders associated with diabetes in warm-blooded animals comprising administering to warm-blooded animals in need thereof an amount of a compound of claim 1 sufficient to treat cardiovascular disorders associated with diabetes.

* * * * *